US008907060B2

(12) United States Patent
Pastan et al.

(10) Patent No.: US 8,907,060 B2
(45) Date of Patent: *Dec. 9, 2014

(54) **MUTATED *PSEUDOMONAS* EXOTOXINS WITH REDUCED ANTIGENICITY**

(75) Inventors: Ira H. Pastan, Potomac, MD (US); Masanori Onda, Rockville, MD (US); Satoshi Nagata, Sioux Falls, SD (US); David Fitzgerald, Rockville, MD (US); Robert Kreitman, Potomac, MD (US); Byungkook Lee, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 1933 days.

This patent is subject to a terminal disclaimer.

(21) Appl. No.: 11/997,202

(22) PCT Filed: Jul. 25, 2006

(86) PCT No.: PCT/US2006/028986
§ 371 (c)(1),
(2), (4) Date: Apr. 8, 2008

(87) PCT Pub. No.: WO2007/016150
PCT Pub. Date: Feb. 8, 2007

(65) Prior Publication Data
US 2009/0142341 A1 Jun. 4, 2009

Related U.S. Application Data

(60) Provisional application No. 60/703,798, filed on Jul. 29, 2005.

(51) Int. Cl.
| | | |
|---|---|---|
| *A61K 38/00* | (2006.01) | |
| *A61K 39/395* | (2006.01) | |
| *C07K 14/21* | (2006.01) | |
| *A61K 47/48* | (2006.01) | |

(52) U.S. Cl.
CPC ....... *A61K 47/48484* (2013.01); *C07K 2319/33* (2013.01); *C07K 14/21* (2013.01); *A61K 38/00* (2013.01)
USPC .................... 530/350; 424/133.1; 424/178.1; 424/190.1; 424/234.1; 424/260.1

(58) Field of Classification Search
CPC .............................. A61K 38/00; A61K 38/43
USPC ...................................................... 424/260.1
See application file for complete search history.

(56) References Cited

U.S. PATENT DOCUMENTS 4,235,871 A    11/1980   Papahadjopoulos et al.
(Continued)

FOREIGN PATENT DOCUMENTS

EP         0404097 A2    12/1990
WO    WO 93/11161 A1     6/1993
(Continued)

OTHER PUBLICATIONS

Katsuri et al 1992 Journal of Biological Chemistry vol. 267 No. 32 Issue of Nov. 15 pp. 23427-23433.*
(Continued)

*Primary Examiner* — Albert Navarro
*Assistant Examiner* — Ginny Portner
(74) *Attorney, Agent, or Firm* — Leydig, Voit & Mayer

(57) ABSTRACT

The invention provides mutated *Pseudomonas* exotoxins (PE) that have reduced immunogenicity compared to PEs containing the native sequence. The PEs of the invention have one or more individual mutations of positions of the native sequence of PE that reduce antibody binding to one or more PE epitopes. Nucleic acids encoding the mutated PEs, chimeric molecules comprising them, compositions comprising the chimeric molecules and methods of using them, are also provided.

105 Claims, 6 Drawing Sheets

(56) References Cited

U.S. PATENT DOCUMENTS

Figure 1:
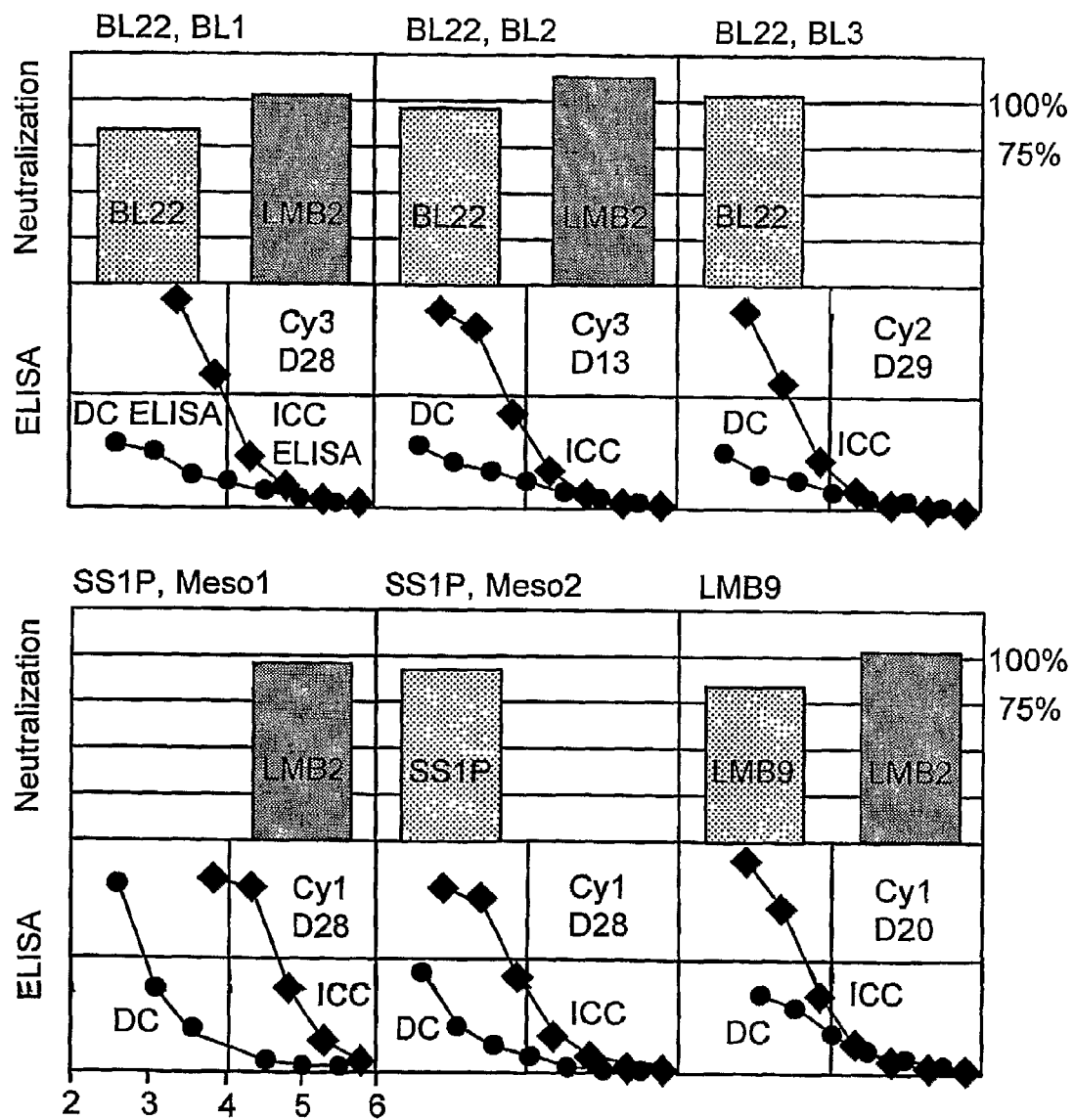

| | | | |
|---|---|---|---|
| 4,458,066 | A | 7/1984 | Caruthers et al. |
| 4,501,728 | A | 2/1985 | Geho et al. |
| 4,837,028 | A | 6/1989 | Allen |
| 4,892,827 | A | 1/1990 | Pastan et al. |
| 4,902,505 | A | 2/1990 | Pardridge et al. |
| 4,957,735 | A | 9/1990 | Huang |
| 5,004,697 | A | 4/1991 | Pardridge |
| 5,019,369 | A | 5/1991 | Presant et al. |
| 5,055,303 | A | 10/1991 | Riley, Jr. |
| 5,188,837 | A | 2/1993 | Domb |
| 5,254,342 | A | 10/1993 | Shen et al. |
| 5,268,164 | A | 12/1993 | Kozarich et al. |
| 5,271,961 | A | 12/1993 | Mathiowitz et al. |
| 5,413,797 | A | 5/1995 | Khan et al. |
| 5,506,206 | A | 4/1996 | Kozarich et al. |
| 5,512,658 | A * | 4/1996 | Pastan et al. .................. 530/350 |
| 5,514,670 | A | 5/1996 | Friedman et al. |
| 5,534,496 | A | 7/1996 | Lee et al. |
| 5,591,828 | A | 1/1997 | Bosslet et al. |
| 5,602,095 | A * | 2/1997 | Pastan et al. .................. 424/780 |
| 5,608,039 | A | 3/1997 | Pastan et al. |
| 5,621,078 | A * | 4/1997 | Riemen et al. ................. 530/350 |
| 5,747,654 | A | 5/1998 | Pastan et al. |
| 5,821,238 | A | 10/1998 | Pastan et al. |
| 5,854,044 | A | 12/1998 | Pastan et al. |
| 5,888,773 | A | 3/1999 | Jost et al. |
| 6,518,061 | B1 | 2/2003 | Puri et al. |
| 6,558,672 | B1 | 5/2003 | Pastan et al. |
| 7,449,189 | B2 * | 11/2008 | Fattom et al. ............ 424/197.11 |
| 8,460,660 | B2 * | 6/2013 | Ho et al. .................... 424/130.1 |
| 8,524,241 | B2 * | 9/2013 | Seed et al. ................. 424/183.1 |
| 2002/0119492 | A1 | 8/2002 | Chirino et al. |
| 2005/0118182 | A1 * | 6/2005 | Pastan et al. ............... 424/178.1 |
| 2010/0215656 | A1 * | 8/2010 | Pastan et al. ............... 424/134.1 |
| 2012/0263674 | A1 * | 10/2012 | Pastan et al. ................. 424/85.1 |
| 2012/0276190 | A1 * | 11/2012 | Fitzgerald .................... 424/450 |
| 2013/0224202 | A1 * | 8/2013 | Ohlfest et al. ............. 424/135.1 |
| 2014/0094417 | A1 * | 4/2014 | Pastan et al. ................. 514/19.3 |

FOREIGN PATENT DOCUMENTS

| | | | | |
|---|---|---|---|---|
| WO | WO 97/15325 | A1 | 5/1997 | |
| WO | WO 98/20135 | A2 * | 5/1998 | |
| WO | WO 99/51643 | A1 | 10/1999 | |
| WO | WO/00/41474 | * | 7/2000 | |
| WO | WO 00/73346 | * | 12/2000 | |
| WO | WO 01/34645 | A2 | 5/2001 | |
| WO | WO 02/069886 | A2 | 9/2002 | |
| WO | WO 03/027135 | A2 | 4/2003 | |
| WO | WO 03/039600 | A1 | 5/2003 | |
| WO | 2005/052006 | * | 6/2005 | ............ C07K 16/28 |
| WO | WO 2005/052006 | A2 | 6/2005 | |

OTHER PUBLICATIONS

Benhar et al 1994 vol. 269 No. 18 pp. 13398-13404.*
Onda, Masanori et al, Bioconjugate Chemistry, 2003, vol. 14, pp. 480-487, Mutants of Immunotoxin Anti-Tac (dsFv)-PE38 with Variable number of lysine residues as Candidates for Site-specific chemical modification. 1. Properties of Mutant Molecules.*
Roscoe, DM et al, Infection and Immunity, vol. 62(11), pp. 5055-5065, Nov. 1994, Primate Antibody Response to Immunotoxin: Serological and Computer Aided Analysis of Epitopes on a Truncated form of *Pseudomonas* Exotoxin.*
Jinno, Yet al, The Journal of Biological Chemistry, vol. 263(26), Sep. 15, 1988, pp. 13203-13207, Mutational Analysis of Domain I of *Psedumonas* Exotoxin.*
Benhar, Itai et al, The Journal of Biological Chemistry, vol. 269(18), May 6, 1994, pp. 13398-13404.*
Li, Mi et al, PNAS, Sep. 1995, vol. 92, pp. 9308-9312.*
Onda, Masanori et al, Journal of Immunology, vol. 177, 2006, pp. 8822-8834, Characterization of B cell epitopes associated with a truncated form of *Pseudomonas* Exotoxin (PE38) used to make immunotoxins for the treatment of cancer.*

Kasturi, Sanjeevaiah et al., "Alanine Scanning Mutagenesis Identifies Surface Amino Acids on Domain II of *Pseudomonas* Exotoxin Required for Cytotoxicity, Proper Folding, and Secretion into Periplasm," *J. Biol. Chem.*, (1992) 267(32):23427-23433.
Cunningham, Brian C. and James A. Wells, "High-resolution epitope mapping of hGH-receptor interactions by alanine-scanning mutagenesis," 1989, *Science*, vol. 244, pp. 1081-1085.
Frankel, Arthur E., "Reducing the immune response to immunotoxins," 2004, *Clinical Cancer Research*, vol. 10, 13-15. [Commentary].
Onda, M., et al., "Characterization of the B cell epitopes associated with a truncated from of *Pseudomonas* exotoxin (PE38) used to make immunotoxins for the treatment of cancer patients," 2006, *J. Immunol.*, vol. 177, pp. 8822-8834.
Roscoe, D.M., et al., "Primate antibody response to immunotoxin: Serological and computer-aided analysis of epitopes on a truncated form of *Pseudomonas* exotoxin," 1994, *Infection and Immunity*, vol. 62(11), pp. 5055-5065.
Roscoe, D.M., et al., "Identification of epitopes on a mutant form of *Pseudomonas* exotoxin using serum from humans treated with *Pseudomonas* exotoxin containing immunotoxins," 1997, *Eur. J. Immunol.*, vol. 27(6), pp. 1459-1468.
Altschul et al., "Basic local alignment search tool," *J. Mol. Biol.*, 215 (3), 403-410 (1990).
Altschul et al., "Gapped BLAST and PSI-BLAST: a new generation of protein database search programs," *Nucl. Acids Res.*, 25 (17), 3389-3402 (1977).
Arndt et al., "Helix-stabilized Fv (hsFv) antibody fragments: substituting the constant domains of a Fab fragment for a heterodimeric coiled-coil domain," *J. Mol. Biol.*, 312 (1), 221-228 (2001).
Beaucage et al., "Deoxynucleoside phosphoramidites—A new class of key intermediates for deoxypolynucleotide synthesis," *Tetra. Lett.*, 22 (20), 1859-1862 (1981).
Brinkmann, "Recombinant immunotoxins: protein engineering for cancer therapy," *Mol. Med. Today*, 2 (10), 439-446 (1996).
Brown et al., "Chemical synthesis and cloning of a tyrosine tRNA gene," Methods *Enzymol.*, 68, 109-151 (1979).
Buchner et al., "A method for increasing the yield of properly folded recombinant fusion proteins: single-chain immunotoxins from renaturation of bacterial inclusion bodies," *Anal. Biochem.*, 205 (2), 263-270 (1992).
Canziani et al., "Kinetic screening of antibodies from crude hybridoma samples using Biacore," *Anal. Biochem.*, 325 (2), 301-307 (2004).
Davies et al., "Antibody VH Domains as Small Recognition Units," *Biotechnology*, 13, 475-479 (1995).
Fults et al., "Sustained-Release of Urease from a Poloxamer Gel Matrix," *J. Parent. Sci. Tech.*, 44 (2), 58-65 (1990).
Ghahroudi et al., "Selection and identification of single domain antibody fragments from camel heavy-chain antibodies," *FEBS Lett.*, 414, 521-526 (1997).
Henikoff et al., "Amino acid substitution matrices from protein blocks," *Proc. Natl. Acad. Sci. USA*, 89 (22), 10915-10919 (1992).
Holliger et al., "Diabodies: small bivalent and bispecific antibody fragments," *Proc. Natl. Acad. Sci. USA*, 90, 6444-6448 (1993).
Holt et al., "Domain antibodies: proteins for therapy," *Trends Biotech.*, 21 (11), 484-490 (2003).
Huse et al., "Generation of a Large Combinatorial Library of the Immunoglobulin Repertoire in Phage Lambda," *Science*, 246, 1275-1281 (1989).
Hwang et al., "Functional domains of *Pseudomonas* exotoxin identified by deletion analysis of the gene expressed in *E. coli*," *Cell*, 48 (1), 129-136 (1987).
Ijntema et al., "Hydroxyapatite microcarriers for biocontrolled release of protein drugs," *Int. J. Pharm.*, 112 (3), 215-224 (1994).
International Preliminary Report on Patentability, Application No. PCT/US2006/028986, dated Jan. 29, 2008.
International Search Report, Application No. PCT/US2006/028986, dated Jun. 8, 2007.
Johnston et al., "Sustained delivery of interleukin-2 from a poloxamer 407 gel matrix following intraperitoneal injection in mice," *Pharm. Res.*, 9 (3), 425-434 (1992).

(56) References Cited

OTHER PUBLICATIONS

Karlin et al., "Applications and statistics for multiple high-scoring segments in molecular sequences," *Proc. Natl. Acad. Sci. USA*, 90, 5873-5787 (1993).

Kondo et al., "Activity of immunotoxins constructed with modified *Pseudomonas* exotoxin a lacking the cell recognition domain," *J. Biol. Chem.*, 263 (19), 9470-9475 (1988).

Kreitman et al., "Complete regression of human B-cell lymphoma xenografts in mice treated with recombinant anti-CD22 immunotoxin RFB4(dsFv)-PE38 at doses tolerated by cynonnolgus monkeys," *Int. J. Cancer*, 81 (1), 148-155 (1999).

Kreitman et al., "Efficacy of the anti-CD22 recombinant immunotoxin BL22 in chemotherapy-resistant hairy-cell leukemia," *New Engl. J. Med.*, 345 (4), 241-247 (2001).

Langer, "Polymer-controlled drug delivery systems," *Acc. Chem. Res.*, 26 (10), 537-542 (1993).

Lauwereys et al., "Potent enzyme inhibitors derived from dromedary heavy-chain antibodies," *EMBO J.*, 17 (13), 3512-3520 (1998).

Merrifield, "Solid Phase Peptide Synthesis. I. The Synthesis of a Tetrapeptide," *J. Am. Chem. Soc.*, 85, 2149-2154 (1963).

Miller et al., "Methods for Calculating Crossreactivity in Immunoassays," *J. Clin. Immunoassay*, 15 (2), 97-107 (1992).

Nagata et al., "Rapid grouping of monoclonal antibodies based on their topographical epitopes by a label-free competitive immunoassay," *J. Immunol. Methods.*, 292 (1-2), 141-151 (2004).

Narang et al., "Improved phosphotriester method for the synthesis of gene fragments," *Methods. Enzymol.*, 68, 90-98 (1979).

Needham-Vandevanter et al., "Characterization of an adduct between CC-1065 and a defined oligodeoxynucleotide duplex," *Nucl. Acids Res.*, 12 (15), 6159-6168 (1984).

Needleman et al., "A General Method Applicable to the Search for Similiarities in the Amino Acid Sequence of Two Proteins," *J. Mol. Biol.*, 48, 443-453 (1970).

Pai et al., "Anti-tumor activities of immunotoxins made of monoclonal antibody B3 and various forms of *Pseudomonas* exotoxin," *Proc. Natl. Acad. Sci. USA*, 88 (8), 3358-3362 (1991).

Pastan, "Targeted therapy of cancer with recombinant immunotoxins," *Biochim. Biophys. Acta*, 1333 (2), C1-C6 (1997).

Pastan et al., "Recombinant immunotoxins in the treatment of cancer," *Methods Mol. Biol.*, 248, 503-518 (2004).

Pearson et al., "Improved tools for biological sequence comparison," *Proc. Natl. Acad. Sci. USA*, 85 (8), 2444-2448 (1988).

Plückthun, "Antibody engineering: advances from the use of *Escherichia coli* expression systems," *Biotechnology*, 9 (6), 545-551 (1991).

Reiter et al., "An antibody single-domain phage display library of a native heavy chain variable region: isolation of functional single-domain VH molecules with a unique interface," *J. Mol. Biol.*, 290 (3), 685-698 (1999).

Robbio et al., "Epitope mapping analysis of apolipoprotein B-100 using a surface plasmon resonance-based biosensor," *Biosens. Bioelectron.*, 16 (9-12), 963-969 (2001).

Salvatore et al., "Improved cytotoxic activity toward cell lines and fresh leukemia cells of a mutant anti-CD22 immunotoxin obtained by antibody phage display," *Clin. Cancer Res.*, 8 (4), 995-1002 (2002).

Saxena et al., "Formation of three-dimensional structure in proteins. I. Rapid nonenzymic reactivation of reduced lysozyme," *Biochemistry*, 9 (25), 5015-5022 (1970).

Siegall et al., "Functional analysis of domains II, Ib, and III of *Pseudomonas* exotoxin," *J. Biol. Chem.*, 264 (24), 14256-14261 (1989).

Smith et al., "Comparison of Biosequences," *Adv. Appl. Math.*, 2, 482-489 (1981).

Vaughan et al., "Human antibodies with sub-nanomolar affinities isolated from a large non-immunized phage display library," *Nat. Biotechnol.*, 14 (3), 309-314 (1996).

Ward et al., "Binding activities of a repertoire of single immunoglobulin variable domain secreted from *Escherichia coli*," *Nature*, 341, 544-546 (1989).

Wedekind et al., "Refined crystallographic structure of *Pseudomonas aeruginosa* exotoxin A and its implications for the molecular mechanism of toxicity," *J. Mol. Biol.*, 314 (4), 823-837 (2001).

Written Opinion of the International Searching Authority, Application No. PCT/US2006/028986, dated Jan. 29, 2008 pp. 1-10.

Yamao et al., "UGA is read as tryptophan in Mycoplasma capricolum," *Proc. Nat'l Acad. Sci. USA*, 82 (8), 2306-2309 (1985).

\* cited by examiner

US 8,907,060 B2

MUTATED PSEUDOMONAS EXOTOXINS WITH REDUCED ANTIGENICITY

CROSS-REFERENCES TO RELATED APPLICATIONS

This application is the U.S. National Stage Application of International Application No. PCT/US2006/028986, filed Jul. 25, 2006, which claims priority from and benefit of U.S. Provisional Application No. 60/703,798, filed Jul. 29, 2005, the contents of which are each hereby incorporated by reference in their entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

In the past several years immunoconjugates have been developed as an alternative therapeutic approach to treat malignancies. Immunoconjugates were originally composed of an antibody chemically conjugated to a plant or a bacterial toxin, a form that is known as an immunotoxin. The antibody binds to the antigen expressed on the target cell and the toxin is internalized causing cell death by arresting protein synthesis and inducing apoptosis (Brinkmann, U., *Mol. Med. Today,* 2:439-446 (1996)). More recently, genes encoding the antibody and the toxin have been fused and the immunotoxin expressed as a fusion protein.

A number of studies have been conducted on immunotoxins which use as the toxic moiety a bacterial toxin known as *Pseudomonas* exotoxin A ("PE"). Typically, the PE has been truncated or mutated to reduce its non-specific toxicity without destroying its toxicity to cells to which it is targeted by the targeting portion of the immunotoxin. Clinical trials are currently underway testing the use of PE-based immunotoxins as treatments for a variety of cancers.

Current PE-based immunotoxins are highly immunogenic. This has not proven to be a problem in the treatment of hematological malignancies, in which the ability of the immune system to mount a response is often compromised. Immunotoxins can typically be administered multiple times to patients with hematological malignancies. Patients with solid tumors, however, usually develop neutralizing antibodies to PE-based immunotoxins within weeks after the first administration. Since many protocols call for a three week period between administration of immunotoxins, the development of the antibodies during this period effectively means that, for solid tumors, usually only one administration can be made of a PE-based immunotoxin before the patient's antibodies render it ineffective. Even a single administration of a PE-based immunotoxin can be highly useful in reducing the patient's tumor burden, in eliminating smaller metastases, and in alleviating symptoms. Nonetheless, it would be desirable to have less antigenic forms of PE-based immunotoxins that would reduce patients' immunogenic responses.

The present invention satisfies these and other needs.

BRIEF SUMMARY OF THE INVENTION

The present invention provides less immunogenic forms of *Pseudomonas* exotoxin A ("PE") and compositions of and methods for using them. In a first group of embodiments, the invention provides isolated PEs having a substitution of alanine, glycine, serine or glutamine in place of an amino acid residue corresponding to an amino acid residue of SEQ ID NO:1 selected from the group consisting of E282, E285, P290, R313, N314, P319, D324, E327, E331, Q332, D403, R412, R427, E431, R432, R458, D461, R467, R505, R513, E522, R538, E548, R551, R576, K590, and L597, provided that when the substitution is of Q332, the residue substituted is not glutamine. In some embodiments, the PE has a substitution of alanine, glycine serine, or glutamine of an amino acid residue corresponding to an amino acid residue of SEQ ID NO:1 selected from the group consisting of P290, R313, N314, D324, E327, E331, Q332, D403, E431, R432, R458, R467, R505, R513, R538, E548, R576, K590, and L597. In some embodiments, the PE has a substitution of alanine, glycine serine, or glutamine of an amino acid residue corresponding to an amino acid residue of SEQ ID NO:1 selected from the group consisting of R313, N314, D324, E327, E331, Q332, R432, R467, R538, and K590. In some embodiments, the PE has a substitution of alanine, glycine or serine of an amino acid residue corresponding to an amino acid residue of SEQ ID NO:1 selected from the group consisting of E282, E285, P290, R313, N314, P319, D324, E327, E331, Q332, D403, R412, R427, E431, R432, R458, D461, R467, R505, R513, E522, R538, E548, R551, R576, K590, and L597. In some embodiments, the PE has a substitution of alanine for an amino acid residue corresponding to an amino acid residue of SEQ ID NO:1 selected from the group consisting of E282, E285, P290, R313, N314, P319, D324, E327, E331, Q332, D403, R412, R427, E431, R432, R458, D461, R467, R505, R513, E522, R538, E548, R551, R576, K590, and L597. In some embodiments, two or more of said amino acid residues corresponding to amino acid residues of SEQ ID NO:1 are substituted. In some embodiments, the PE further has a substitution of alanine, valine, glycine, leucine, isoleucine or glutamine of arginine at a position corresponding to amino acid residue 490 of SEQ ID NO:1. In some embodiments, alanine is substituted for said amino acid residue 490 of SEQ ID NO:1. In some embodiments, the PE is selected from the group consisting of PE35, PE38, PE38 KDEL, PE40, PE4E, and PE38QQR. In some embodiments, the PE comprises mutations of alanine, valine, glycine, leucine, or isoleucine for the residues corresponding to amino acid residues Q332, R490, R467, and K590 of SEQ ID NO:1. In some embodiments, the PE further comprises a mutation of alanine, valine, glycine, leucine, isoleucine or glutamine at an amino acid residue corresponding to amino acid residue R313 of SEQ ID NO:1. In some embodiments, the PE further comprises a substitution of an amino acid residue corresponding to amino acid residue R432 of SEQ ID NO:1. In some embodiments, the PE further comprises a substitution of an amino acid residue corresponding to amino acid residue R513 of SEQ ID NO.:1. In some embodiments, the PE further comprises a substitution of an amino acid residue corresponding to amino acid residue E548 of SEQ ID NO.:1. In some embodiments, the PE comprises the following substitutions of amino acid residues corresponding to amino acid residues of SEQ ID NO.: 1: R313A, Q332S, R432G, R467A, R490A, R513A, E548S, and K590S.

In a second group of embodiments, the invention provides chimeric molecules comprising (a) a targeting moiety conjugated or fused to (b) a *Pseudomonas* exotoxin A ("PE"), wherein the PE has a substitution of alanine, glycine, serine or glutamine in place of an amino acid residue corresponding to an amino acid residue of SEQ ID NO:1 selected from the group consisting of E282, E285, P290, R313, N314, P319, D324, E327, E331, Q332, D403, R412, R427, E431, R432, R458, D461, R467, R505, R513, E522, R538, E548, R551, R576, K590, and L597, provided that when the substitution is of Q332, the residue substituted for Q332 is not glutamine. In some embodiments, the PE has a substitution of alanine, glycine serine, or glutamine of an amino acid residue corresponding to an amino acid residue of SEQ ID NO:1 selected from the group consisting of P290, R313, N314, D324, E327, E331, Q332, D403, E431, R432, R458, R467, R505, R513, R538, E548, R576, K590, and L597. In some embodiments, the PE has a substitution of alanine, glycine serine, or glutamine of an amino acid residue corresponding to an amino acid residue of SEQ ID NO:1 selected from the group consisting of R313, N314, D324, E327, E331, Q332, R432, R467, R538, and K590. In some embodiments, the PE has a substitution of alanine, glycine or serine of an amino acid residue corresponding to an amino acid residue of SEQ ID NO:1 selected from the group consisting of E282, E285, P290, R313, N314, P319, D324, E327, E331, Q332, D403, R412, R427, E431, R432, R458, D461, R467, R505, R513, E522, R538, E548, R551, R576, K590, and L597. In some embodiments, the PE has a substitution of alanine or serine for an amino acid residue corresponding to an amino acid residue of SEQ ID NO:1 selected from the group consisting of E282, E285, P290, R313, N314, P319, D324, E327, E331, Q332, D403, R412, R427, E431, R432, R458, D461, R467, R505, R513, E522, R538, E548, R551, R576, K590, and L597. In some embodiments, two or more of said amino acid residues corresponding to amino acid residues of SEQ ID NO:1 are substituted. In some embodiments, the PE further has a substitution of alanine, valine, glycine, leucine, isoleucine or glutamine in place of arginine at a position corresponding to amino acid residue 490 of SEQ ID NO:1. In some embodiments, alanine is substituted for said amino acid residue 490 of SEQ ID NO:1. In some embodiments, the PE is selected from the group consisting of PE35, PE38, PE38 KDEL, PE40, PE4E, and PE38QQR. In some embodiments, the PE comprises a substitution of alanine, valine, glycine, leucine, or isoleucine for the residues corresponding to amino acid residues Q332, R490, R467, and K590 of SEQ ID NO:1. In some embodiments, the PE further comprises a substitution of alanine, valine, glycine, leucine, isoleucine or glutamine for an amino acid residue corresponding to amino acid residue R313 of SEQ ID NO:1. In some embodiments, the PE further comprises a substitution of an amino acid residue corresponding to amino acid residue R432 of SEQ ID NO:1. In some embodiments, the PE further comprises a substitution of an amino acid residue corresponding to amino acid residue R513 of SEQ ID NO.:1. In some embodiments, the PE further comprises a substitution of an amino acid residue corresponding to amino acid residue E548 of SEQ ID NO.:1. In some embodiments, the PE comprises the following mutations of amino acid residues corresponding to amino acid residues of SEQ ID NO.: 1: R313A, Q332S, R432G, R467A, R490A, R513A, E548S, and K590S. In some embodiments, the targeting moiety of the chimeric molecule is an antibody. In some embodiments, the antibody is a scFv, a dsFv, or a diabody. In some embodiments, the targeting moiety is a cytokine.

In yet another group of embodiments, the invention provides compositions comprising (a) any of the above-described chimeric molecules, and (b) a pharmaceutically acceptable carrier.

In still another group of embodiments, the invention provides isolated nucleic acids encoding a modified *Pseudomonas* exotoxin A ("PE"), wherein the PE has a substitution of alanine, valine, glycine, leucine, isoleucine or glutamine in place of an amino acid residue corresponding to an amino acid residue of SEQ ID NO:1 selected from the group consisting of E282, E285, P290, R313, N314, P319, D324, E327, E331, Q332, D403, R412, R427, E431, R432, R458, D461, R467, R505, R513, E522, R538, E548, R551, R576, K590, and L597, provided that when the substitution is of Q332, the residue substituted is not glutamine. In some embodiments, the PE has a substitution of alanine, glycine serine, or glutamine of an amino acid residue corresponding to an amino acid residue of SEQ ID NO:1 selected from the group consisting of P290, R313, N314, D324, E327, E331, Q332, D403, E431, R432, R458, R467, R505, R513, R538, E548, R576, K590, and L597. In some embodiments, the PE has a substitution of alanine, glycine serine, or glutamine of an amino acid residue corresponding to an amino acid residue of SEQ ID NO:1 selected from the group consisting of R313, N314, D324, E327, E331, Q332, R432, R467, R538, and K590. In some embodiments, the PE has a substitution of alanine, glycine or serine of an amino acid residue corresponding to an amino acid residue of SEQ ID NO:1 selected from the group consisting of E282, E285, P290, R313, N314, P319, D324, E327, E331, Q332, D403, R412, R427, E431, R432, R458, D461, R467, R505, R513, E522, R538, E548, R551, R576, K590, and L597. In some embodiments, the PE has a substitution of alanine for an amino acid residue corresponding to an amino acid residue of SEQ ID NO:1 selected from the group consisting of E282, E285, P290, R313, N314, P319, D324, E327, E331, Q332, D403, R412, R427, E431, R432, R458, D461, R467, R505, R513, E522, R538, E548, R551, R576, K590, and L597. In some embodiments, two or more of said amino acid residues corresponding to amino acid residues of SEQ ID NO:1 are substituted. In some embodiments, the PE further has a substitution of alanine, valine, glycine, leucine, isoleucine or glutamine of arginine at a position corresponding to amino acid residue 490 of SEQ ID NO:1. In some embodiments, alanine is substituted for said amino acid residue 490 of SEQ ID NO:1. In some embodiments, the PE is selected from the group consisting of PE35, PE38, PE38 KDEL, PE40, PE4E, and PE38QQR. In some embodiments, the PE comprises mutations of alanine, valine, glycine, leucine, or isoleucine for the residues corresponding to amino acid residues Q332, R490, R467, and K590 of SEQ ID NO:1. In some embodiments, the PE further comprises a mutation of alanine, valine, glycine, leucine, isoleucine or glutamine at an amino acid residue corresponding to amino acid residue R313 of SEQ ID NO:1. In some embodiments, the PE further comprises a substitution of an amino acid residue corresponding to amino acid residue R432 of SEQ ID NO:1. In some embodiments, the PE further comprises a substitution of an amino acid residue corresponding to amino acid residue R513 of SEQ ID NO.:1. In some embodiments, the PE further comprises a substitution of an amino acid residue corresponding to amino acid residue E548 of SEQ ID NO.:1. In some embodiments, the PE comprises the following substitutions of amino acid residues corresponding to amino acid residues of SEQ ID NO.: 1: R313A, Q332S, R432G, R467A, R490A, R513A, E548S, and K590S. In some embodiments, the nucleic acid is operably linked to a promoter.

In yet another group of embodiments, the invention provides methods of inhibiting the growth of a cell bearing a target molecule, said method comprising contacting said cell with a chimeric molecule comprising (a) a targeting moiety that specifically binds said target molecule, and (b) a *Pseudomonas* exotoxin A ("PE"), wherein the PE has a substitution of alanine, valine, glycine, leucine, isoleucine or glutamine in place of an amino acid residue corresponding to an amino acid residue of SEQ ID NO:1 selected from the group consisting of E282, E285, P290, R313, N314, P319, D324, E327, E331, Q332, D403, R412, R427, E431, R432, R458, D461, R467, R505, R513, E522, R538, E548, R551, R576, K590, and L597, provided that when the residue being substituted corresponds to Q332, the amino acid substituted is not glutamine, wherein contacting said cell with said chimeric molecule inhibits the growth of said cell. In some embodiments, the substitution is for an amino acid residue corresponding to an amino acid residue of SEQ ID NO:1 selected from the group consisting of P290, R313, N314, D324, E327, E331, Q332, D403, E431, R432, R458, R467, R505, R513, R538, E548, R576, K590, and L597. In some embodiments, the substitution is of an amino acid residue corresponding to an amino acid residue of SEQ ID NO:1 selected from the group consisting of R313, N314, D324, E327, E331, Q332, R432, R467, R538, and K590. In some embodiments, the substitution is of an alanine or serine in place of an amino acid residue corresponding to an amino acid residue of SEQ ID NO:1 selected from the group consisting of E282, E285, P290, R313, N314, P319, D324, E327, E331, Q332, D403, R412, R427, E431, R432, R458, D461, R467, R505, R513, E522, R538, E548, R551, R576, K590, and L597. In some embodiments, the substitution is of alanine in place of an amino acid residue corresponding to an amino acid residue of SEQ ID NO:1 selected from the group consisting of E282, E285, P290, R313, N314, P319, D324, E327, E331, Q332, D403, R412, R427, E431, R432, R458, D461, R467, R505, R513, E522, R538, E548, R551, R576, K590, and L597. In some embodiments, the PE further has a substitution of alanine, valine, glycine, leucine, isoleucine or glutamine in place of an amino acid residue corresponding to amino acid residue R490 of SEQ ID NO:1. In some embodiments, the PE has an alanine in place of an amino acid residue corresponding to amino acid residue R490 of SEQ ID NO:1. In some embodiments, the PE is selected from the group consisting of PE35, PE38, PE38 KDEL, PE40, PE4E, and PE38QQR. In some embodiments, the target molecule is a cytokine receptor and said targeting moiety is a cytokine which binds to said receptor. In some embodiments, the target molecule is an IL-13 receptor and said targeting molecule is a IL-13, a mutated IL-13, or a circularly permuted IL-13. In some embodiments, the target molecule is an antigen and said targeting molecule is an antibody which specifically binds to said antigen. In some embodiments, the antigen is a cancer antigen. In some embodiments, the PE comprises substitutions at positions corresponding to Q332, R490, R467, and K590 of SEQ ID NO.: 1. In some embodiments, the PE further comprises a substitution at a position corresponding to R313 of SEQ ID NO.:1. In some embodiments, the PE further comprises a substitution at a position corresponding to R432 of SEQ ID NO.:1. In some embodiments, the PE further comprises a substitution at a position corresponding to R513 of SEQ ID NO.:1. In some embodiments, the PB further comprises a substitution at a position corresponding to E548 of SEQ ID NO.:1. In some embodiments, the PE has the following substitutions of positions corresponding to R313A, Q332S, R432G, R467A, R490A, R513A, E548S, and K590S of SEQ ID NO.: 1.

BRIEF DESCRIPTION OF THE DRAWINGS

FIG. 1 shows representative data of antibody responses in patients treated with three different immunotoxins, BL22, SS1P, LMB9. Each immunotoxin contains an antibody portion, which is different for each immunotoxin; each uses PE38 as the toxic moiety. Serum samples collected from patients and tested for neutralizing activity in a cell killing assay (bar graphs) and its reactivity with immunotoxins in different ELISAs (line graphs). The immunotoxin with which the patient was treated, and in most cases, the cancer which the patient had, is listed at the top of each panel. The number of cycles of treatment the patient had before serum collection and the days after the last treatment are shown in the line graph panels. Line graphs show the antibody in the serum samples measured by two different ELISAs. ICC-ELISA can measure antibodies reacting with native PE.

FIG. 2 shows the results of topographical epitope mapping based on mutual competition of all possible pairs of the antibodies produced in the course of the studies reported herein. The darker the shade, the stronger the competition. Thus, very dark shading indicates very strong competition, while very light shadings indicates no competition.

FIG. 3 is a Biacore sensorgram showing the additive binding of monoclonal antibodies ("MAbs") assigned to different epitope groups.

FIG. 4 is a table showing the effect of 45 different point mutations in PE. The Y axis lists the epitopes and subepitopes of PE, except for subepitope 2a. The next column on the Y axis provides the number of an antibody which was found in competition studies to bind to the indicated epitope or subepitope. The row across the top of the X axis shows each mutation. "WT" stands for "wild-type" and refers to unmutated PE38. At the far right, under the word Domains, Domains II and III are seen. PE38 does not contain PE domain I.

FIG. 5 shows that the $IC_{50}$ for an immunotoxin in which the toxic moiety is a mutant PE in which 7 mutations were made (referred to as the "7×" mutant) to destroy particular epitopes and the $IC_{50}$ for the same immunotoxin in which the toxic moiety is the 7× mutant with yet an additional mutation (referred to as the "8×" mutant) are close to the $IC_{50}$ of the starting HA22 immunotoxin.

FIG. 6 shows the results of an in vivo study of human tumor xenografts in scid mice. "CA46" is a lymphoma that grows subcutaneously as a solid tumor in mice. The tumor cells were introduced into the mice on day 0 and mice were administered the immunotoxin on days 8, 10 and 12, as indicated by the arrows on the X axis. The size of the tumors is shown on the Y axis. Legend: Squares represent the control (vehicle). Diamonds represent the immunotoxin HA22, an anti-CD22 immunotoxin which uses PE38 as the toxic moiety. Triangles: HA22-8M. HA22-8M is HA22 immunotoxin in which eight mutations have been made in the PE38 molecule to reduce immunogenicity. The eight mutations are R313A, Q332S, R432G, R467A, R490A, R513A, E548S, and K590S, wherein the numbers designate the residue having that position in SEQ ID NO.:1.

DETAILED DESCRIPTION OF THE INVENTION

Introduction

For over 15 years, *Pseudomonas* exotoxin A ("PE") has been investigated for use as the toxic portion of chimeric molecules such as immunotoxins. That work is embodied in the development of a number of mutated forms of PE in which cytotoxic activity has been retained, while non-specific toxicity of the molecule has been reduced or eliminated. Most of these mutants have been truncated to improve their tumor penetration. Some have also had modifications in addition to truncation, such as modifying the carboxyl terminal residues or eliminating the requirement for cleavage between residues 279 and 280 by the protease furin, to increase their cytotoxicity. Immunotoxins using mutated forms of PE have shown considerable therapeutic promise in human clinical trials.

The use of PE-based immunotoxins for treatment of solid tumors in particular, however, has been limited because of the development of neutralizing antibodies to the immunotoxin after the first administration. These antibodies develop before most protocols would call for a second administration of the immunotoxin, and therefore render further use of the immunotoxins-ineffective against solid tumors in previously exposed-patients.

The studies underlying the present invention reveal that the predominant immune response of patients to PE-based immunotoxins is to the PE portion of the immunotoxin. This understanding indicates that reducing the antigenicity of the PE molecules used for immunotoxins would reduce the overall antigenicity of the immunotoxin, and increase their utility. The studies underlying the present invention further reveal that PE has seven major epitopes, which can be further divided into a total of thirteen subepitopes.

Surprisingly, it has been discovered that, for ten of the thirteen subepitopes of PE, the antigenicity of the epitope or subepitope can be reduced or eliminated by mutating a single amino acid residue of PE. Of course, since PE contains a multiplicity of antigenic epitopes, no single mutation eliminates the antigenicity of the whole PE molecule. Each individual mutation of the present invention, however, reduces the antigenicity of an individual epitope or subepitope. The individual mutations therefore reduce the antigenicity of the overall PE molecule and any immunotoxin made with the mutated PE.

The studies underlying the invention have further demonstrated that various of the mutations can be combined to reduce the overall antigenicity of the molecule while retaining the cytotoxicity of the PE molecule. PE molecules were made in which 3, 4, 5, 6, 7, or 8 residues of different epitopes or subepitopes were mutated. The PEs with the mutations were made into immunotoxins, and their cytotoxicity assayed. For ease of comparison, the PEs were made into immunotoxins each of which used the same targeting moiety (a high affinity, anti-CD22 antibody). Further, to facilitate comparison, the PE38 form of PE was used as the PE in which the substitutions were made. Given our experience with many PE-based immunotoxins over the past 15 years, the fact that all cytotoxic forms of PE share the same mechanism of cytotoxicity to target cells (ADP-ribosylation of elongation factor 2), and the fact that the other variants of PE in use are simply the same amino acid sequence with particular truncations (or, in the case of PE4E, four mutations in domain Ia, rather than a truncation), the results obtained with PE38 are expected to be directly applicable to other forms of PE (such as the exemplar forms known respectively as PE40, PE38, PE37, PE35, PE4E, PE38QQR, and PE38 KDEL, described in more detail below).

It is expected that, as immunotoxins, the mutated PEs already made, and others modified according to the teachings of the present invention, will, when made into immunotoxins, provoke less of an immune response in vivo, and that this lessened immune response will be reflected by lower titers of neutralizing antibodies. The development of neutralizing antibodies is routinely assayed in preclinical testing of immunotoxins and in immunotoxin clinical trial protocols, and the antibody titers induced by immunotoxins made using the PEs of the invention can be measured by these standard assays.

Persons of skill will appreciate that the PEs of the invention will be as useful as the mutated PEs previously known which have been made into immunotoxins and tested in clinical trials. As noted, however, immunotoxins made with the PEs of the invention are expected to display less antigenicity than do immunotoxins made with currently available PE molecules, and to thereby provoke less of an immune response in patients than do currently available PE-based immunotoxins.

The mutations of the present invention can be easily engineered into already-modified PEs (such as the exemplar forms known respectively as PE40, PE38, PE37, PE35, PE4E, PE38QQR, and PE38 KDEL, described in more detail below) to reduce their antigenicity, and thereby reduce patients' immunogenic responses to immunotoxins containing them. Accordingly, the invention provides an important new means of increasing the therapeutic utility of PE-based immunoconjugates, such as the various PE-based immunotoxins currently in clinical trials.

As noted, the improved PEs of the invention comprise mutations of the molecule at specific positions of the PE molecule. By convention, positions in PE and its variants are notated in the art by reference to the corresponding position in the 613 amino acid sequence of the native PE molecule (SEQ ID NO.:1). This convention is followed herein to permit ready comparison among PE variants and to promote understanding which residues are mutated in the PEs of the invention. For example, as discussed in more detail below, in most clinically useful forms of PE, domain Ia (amino acids 1-252) of the molecule is deleted to reduce non-specific binding. A PE with domain Ia deleted has only 361 residues. Nonetheless, a reference herein to Q332 refers to the glutamine found at position 332 of the native PE sequence, regardless of the number of that residue if counted from the amino terminus of the particular PE in which it occurs, while R590 refers to the lysine found at position 590 of native PE and so on. The amino acid sequence of native PE (SEQ ID NO.: 1) is well known in the art and is set forth, for example, in U.S. Pat. No. 5,602,095.

As indicated below, in preferred embodiments, in the compositions and methods of the invention, the amino acid residue present in the native sequence of PE at the positions identified herein is replaced by an amino acid selected from the group alanine, glycine, serine or glutamine. Alanine, glycine and serine are particularly preferred as the replacement residues, with alanine and serine being particularly preferred.

To be useful, the PE must retain cytotoxic activity following the substitutions of the residues. To test the retention of cytotoxicity by PEs altered to reduce their antigenicity, a number of exemplar immunotoxins have been made. In a first series of studies, nineteen immunotoxins were made. To permit comparison, each of these immunotoxins used the same targeting moiety and each started with the same truncated form of PE known as PE38. In each of the nineteen immunotoxins, a different residue of PE38 was replaced by a mutation identified as reducing the antigenicity of a particular PE epitope or subepitope. The cytotoxic activity of these nineteen mutated PE38s was then compared to an immunotoxin made with the same targeting moiety and with unaltered PE38 (which for convenience will be called the "wild type" immunotoxin).

As shown in Table 3, below, assays of the cytotoxicity of the immunotoxins showed that twelve of the exemplar experimental immunotoxins actually had higher cytotoxicity than did the immunotoxin made with the wild type PE38 sequence, while two had approximately the cytotoxicity of the wild type immunotoxin. Remarkably, several of the immunotoxins made with the experimental exemplar PEs actually showed cytotoxicity 50% or more greater than that of the immunotoxin made with the wild type PE38 sequence. Thus, this series of studies showed not only that a number of the mutations of the invention could be made without any loss of cytotoxicity of the resulting immunotoxin, but that several actually increased it.

Five of the immunotoxins in the initial studies showed less cytotoxicity than did the immunotoxin using the PE38 sequence usually used in the art, but still retained considerable cytotoxic activity. While more cytotoxicity is usually preferable to less, in practice the reduced cytotoxicity of these mutated forms of PE is expected to be offset to at least some degree by the reduced antigenicity of immunotoxins made with them. Thus, even these PEs with reduced cytotoxicity may be useful for some applications. Moreover, coupled with a PE mutation that exhibits increased cytotoxicity when made into an immunotoxin, the cytotoxicity of the PE may be closer to that of the wild type PE. And, since PE is a very potent cytotoxin, even mutated forms of PE with toxicity considerably reduced from that of the native toxin retain considerable power as toxic moieties.

The studies underlying the invention revealed amino acids whose replacement decreased at least 5-fold, more preferably at least 10-fold, and most preferably at least 20-fold, the binding to more than two monoclonal antibodies ("MAbs") assigned to the same epitope. It is expected that the reduction of binding of MAbs to the epitope correlates with a loss of antigenicity of the epitope, and therefore of PE molecules containing the mutation.

The positions of PE at which mutations were found to reduce binding of MAbs to the same epitope by at least 5-fold were E282, E285, P290, R313, N314, P319, D324, E327, E331, Q332, D403, R412, R427, E431, R432, R458, D461, R467, R490, R505, R513, E522, R538, E548, R551, R576, K590, and L597. The positions of PE at which mutations were found to reduce binding of MAbs to the same epitope by at least 10-fold were E282, E285, P290, R313, N314, D324, E327, E331, Q332, D403, R412, E431, R427, R432, R458, D461, R467, R490, R505, R513, E522, R538, E548, R576, and R590. The positions of PE at which mutations were found to reduce binding of MAbs to the same epitope by at least 20-fold were N314, D324, E327, E331, Q332, D403, R432, R467, R490, R505, R513, R538, R551, K590, and L597.

Figure 4:
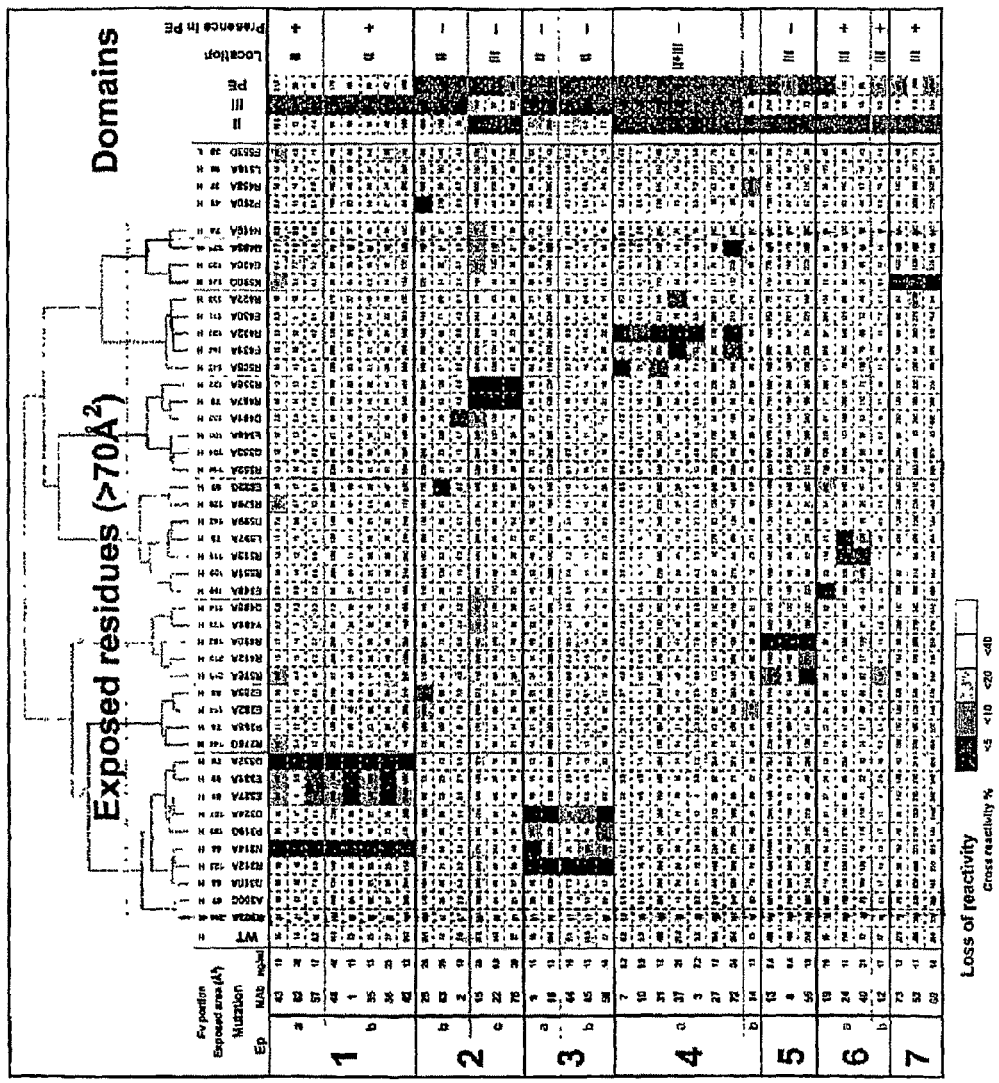

Each of these mutations reduces binding of MAbs to a particular epitope or subepitope of PE, as can be determined by reference to FIG. 4. It is expected that combining replacement any one of these mutations (which may conveniently be referred to as mutation "A") with the mutation of one or more residues that reduce binding to one of the epitopes or subepitopes of PE other than the epitope or subepitope as to which mutation A reduces binding will further reduce the antigenicity of the molecule and the development of antibodies to the PE portion of an immunotoxin made with the resulting PE. Conversely, it is not typically necessary to mutate more than one residue that FIG. 4 shows eliminates antigenicity of an entire epitope. Where FIG. 4 shows no single mutation eliminates binding of all antibodies to an epitope, it may be desirable to combine mutations to eliminate binding to that epitope. For example, to eliminate all binding to epitope 6a, it may be desirable to combine in a single PE of the invention E548A and R513A, and to reduce binding to epitope 6b, to further combine with these mutations the mutation R576A.

In previous studies by the laboratory of the present inventors, reported in PCT application PCT/US2004/039617 (International Publication WO 2005/052006), it was discovered that mutating PE residue R490 to alanine doubled the cytotoxicity of the resulting PE molecule when used as the toxin moiety of an immunotoxin. Surprisingly, the studies underlying the present invention show that mutation of the arginine at PE position 490 also eliminates antibody binding to PE epitope 5. Therefore, replacement of the arginine at position 490 of PE with one of the residues discussed above is expected to decrease the antigenicity of the PE molecule. It is further expected that combining replacement of the arginine at PE position 490 with the replacement of one or more residues that reduce binding to one of the epitopes or subepitopes of PE other than epitope 5 will further reduce the antigenicity of the molecule and the development of antibodies to the PE portion of an immunotoxin made with the resulting PE. It is noted that no mutations were found that reduced binding to subepitope 2a; accordingly, this subepitope is not shown in FIG. 4.

WO 2005/052006 further indicates that the arginine at position 490 of PE can be mutated to glycine, alanine, valine, leucine, or isoleucine. Increased cytotoxic activity and decreased immunogenicity are separate phenomena. Therefore, not all mutations that are expected to result in increased cytotoxic activity are also expected to result in decreased immunogenicity. Mutations that do both, such as mutations of R490 to glycine or, more preferably, alanine, are particularly desirable.

Surprisingly, it has now been discovered that certain other residues can be mutated and also result in PEs which can be made into immunotoxins with cytotoxicity at least the same, and in some cases significantly greater than that of PE38. As shown in Table 3, set forth following the Examples, below, mutating R313, E327, E331, Q332, E431, R432, R505, R516, R538, and K590 also resulted in immunotoxins with cytotoxicity greater than that of the like immunotoxin made with PE38. Since it is likely that immunotoxins with increased cytotoxicity will exhibit increased ability to kill target cells, or permit dosing a patient with a smaller amount of immunotoxin to achieve the same therapeutic effect, these mutations would be advantageous even if none of them also reduced antigenicity of the PE molecule. Since, however, each of these mutations, and that of R490, also each reduce antigenicity of PE, it is desirable to combine one or more of these mutations in a single PE. As with other combinations of mutations of the invention, it is particularly desirable to combine mutations which reduce or eliminate antigenicity of different epitopes or subepitopes. For example, one desirable combination of mutations is to mutate Q332 (which reduces antigenicity of subepitopes 1a and b), and R467 (which reduces antigenicity of subepitope 2c), in addition to R490 (which, as noted, eliminates antigenicity of epitope 5).

In a further group of experiments, studies were undertaken to confirm that combining mutations expected to reduce the immunogenicity of the overall PE molecule could be made while retaining strong cytotoxicity. Since PE38 is the form of PE that has been subjected to the most clinical testing, it is the one that was used in the studies reported herein. Since all the variants of PE are truncations or mutated versions of the same protein, and all share the same enzymatic activity, it is expected that the results obtained with PE38 will obtain for other variants of PE, such as PE35, PE37, PE38QQR, PE40, PE4E, and variations of these which have particular mutations at the carboxyl terminal, as described in more detail below.

Table 4, below, reports the results of studies on a number of single and multiple mutations of PE. For example, a series of combinations were made to reduce the immunogenicity of various epitopes of PE. As each combination of mutations was tested for cytotoxicity, an additional mutation was added to reduce immunogenicity of an additional epitopes or subepitope of PE.

For example, Table 4 reports the results of studies of the cytotoxicity of a four-mutation mutant of PE, in which the following mutations were made: ☐332S R490A R467A K590S, to reduce the immunogenicity of epitopes 1, 2c, 5, and 7. A five-mutation mutant was made by adding a mutation at position R313 to reduce the immunogenicity of epitope 3, as follows: R313A Q332S R467A R490A K590S; this mutant was tested in two cytotoxicity assays. A six-mutation mutant was then made by adding to this mutant a mutation of R432G to reduce the immunogenicity of epitope 4a, while a seven mutation mutant was made by adding R513A to reduce the immunogenicity of an additional epitope. Finally, an eight-mutation mutant was made with the following mutations: R313A Q332S R432G R467A R490A R513A E548S K590S, to reduce the immunogenicity of a subepitope of epitope 6; the cytotoxicity of the eight-mutation mutant was tested and found to be close to that of the starting immunotoxins (the starting immunotoxin is known as HA22). The results on cytotoxicity of these mutations are shown in Table 4. Given the results with these exemplar combinations of mutations, it is expected that other combinations of the mutations shown on FIG. 4 can be made to reduce the immunogenicity of the various epitopes and subepitopes of PE and will retain adequate cytotoxicity to be useful as the toxic portion of immunotoxins.

In the course of these studies, it was found that some mutations to alanine that resulted in highly cytotoxic immunotoxins by themselves seemed to result in some loss of activity when combined with multiple mutations in which the other residues were also mutated to alanine. It was speculated that this was due to the presence of too many alanine mutations, making the molecule as a whole too hydrophobic. To counter this, some of the residues were mutated to serine instead of alanine; and cytotoxicity was restored. Glycine can also be used in such circumstances, and other residues can be mutated to serine rather than the two selected in these studies. It is expected that selecting other residues for mutation to serine instead of alanine would also be effective since what is important is too avoid creating too much hydrophobicity; this goal can be accomplished by, for example, mutating R313 to serine while leaving Q332 mutated to A, and so on. The practitioner can readily test any particular desired combination of the desirable mutations taught herein to confirm whether or not the combination retains cytotoxic capability.

Table 4 also shows that some specific mutations resulted in some loss of cytotoxicity. For example, the mutation N314A resulted in the loss of more than 50% of the cytotoxicity. Since PE is such an active cytotoxin, this mutation would still be useful. Table 4 also shows, however, that while the mutant R490A retains at least the activity of the starting PE38 molecule, the mutant R490S has little activity, and is not preferred. Mutation of R538 to alanine results in some, but acceptable, loss of activity, while mutation of the same residue to serine results in a sharp loss of activity, and is not preferred. Once again, the practitioner can readily test any particular desired combination of the desirable mutations taught herein to confirm whether or not the combination retains cytotoxic capability.

Persons of skill are aware that various types of molecules can serve as a basis of targeting PEs containing the mutations of the invention to cells that the practitioner wishes to kill or to inhibit. As evident from the discussion above, antibodies are one especially preferred type of targeting agent.

In another preferred embodiment, the targeting portion, or moiety, of the chimeric molecule is a cytokine, which can be used to target toxins to cells overexpressing a receptor for the cytokine. IL-13 receptors, for example, are known to be heavily overexpressed on the exterior of cells of certain cancers, such as gliomas, and to act as an autocrine growth factor on such cancers as renal cell carcinoma, Kaposi's sarcoma, and Hodgkin's disease. See, e.g., WO 01/34645, WO 03/039600 and U.S. Pat. No. 6,518,061. IL-13 or various mutants and circularly permuted forms of IL-13 can be used to target cytotoxins, such as PE molecules containing one or more mutations of the invention to cells expressing the IL-13 receptor. Further, the various forms of IL-13, including circularly permuted forms, can be used to target PE molecules with the mutations to cells in the lungs expressing IL-13 receptor to reduce or end symptoms in conditions, such as asthma and allergic rhinitis, and to cells elsewhere in the body to reduce or end symptoms of atopic dermatitis, and hepatic fibrosis in schistosomiasis, as discussed in international publication WO 01/34645.

In addition to cytokines, numerous other ligands are known in the art and can be used for targeting PE molecules of the invention to target cells. For example, transferrin has been used as a means of targeting toxins to cells expressing transferrin receptors. Similarly, cells involved in a disease or condition can be targeted if there is an antigen on the cell surface that is specifically or preferentially expressed in cells related to the disease or condition, such as gp120 in HIV-infected cells, CD25 on T cells that are involved in graft versus host disease or various surface molecules that are expressed on cancer cells, such as CEA, CD30, or CD33.

Definitions

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

*Pseudomonas* exotoxin A ("PE") is an extremely active monomeric protein (molecular weight 66 kD), secreted by *Pseudomonas aeruginosa*, which inhibits protein synthesis in eukaryotic cells. The native PE sequence (SEQ ID NO.:1) is set forth in U.S. Pat. No. 5,602,095, incorporated herein by reference. The method of action and structure of PE, as well as the modifications resulting in a number of variants of PE, are discussed in some detail in a section devoted to this purpose within.

Mutations of PE are described herein by reference to the amino acid residue present at a particular position of the 613-amino acid sequence of native PE (SEQ ID NO:1), followed by the amino acid with which that residue has been replaced in the particular mutation under discussion. Thus, for example, the term "R490A" indicates that the "R" (arginine, in standard single letter code) at position 490 of the referenced molecule is replaced by an "A" (alanine, in standard single letter code), while "K590Q" indicates that the lysine normally present at position 590 has been replaced with a glutamine. The standard single letter code for common amino acids is set forth below.

"BL22" (or "RFB-4(dsFv)-PE38") is an immunotoxin employing as the targeting moiety a disulfide-stabilized Fv region of the anti-C22 antibody known in the art as "RFB-4". The sequence of the RFB-4 antibody is well known in the art. BL22 is described in Kreitman et al., New Eng J Med 345(4): 241-7 (2001). The BL22 immunotoxin uses PE38 as the toxic portion of the immunotoxin.

"HA22" is an immunotoxin employing as the targeting moiety a mutated form of RFB-4 in which residues SSY of CDR3 of the variable heavy chain have been mutated to THW. This mutation of RFB-4 and its effect on immunotoxins employing it as the targeting moiety are described in International Publication WO 03/027135 and Salvatore et al., Clin Cancer Res 8(4):995-1002 (2002). The HA22 immunotoxin uses PE38 as the toxic portion of the immunotoxin.

For convenience of reference, as used herein, the term "antibody" includes whole (sometimes referred to herein as "intact") antibodies, antibody fragments that retain antigen recognition and binding capability, whether produced by the modification of whole antibodies or synthesized de novo using recombinant DNA methodologies, monoclonal antibodies, polyclonal antibodies, and antibody mimics, unless otherwise required by context. The antibody may be an IgM, IgG (e.g. $IgG_1$, $IgG_2$, $IgG_3$ or $IgG_4$), IgD, IgA or IgE.

The term "antibody fragments" means molecules that comprise a portion of an intact antibody, generally the antigen binding or variable region of the intact antibody. Examples of antibody fragments include Fab, Fab', $F(ab')_2$, and Fv fragments; helix-stabilized antibodies (see, e.g., Arndt et al., J Mol Biol 312:221-228 (2001); diabodies (see below); single-chain antibody molecules ("scFvs," see, e.g., U.S. Pat. No. 5,888,773); disulfide stabilized antibodies ("dsFvs", see, e.g., U.S. Pat. Nos. 5,747,654 and 6,558,672), and domain antibodies ("dAbs," see, e.g., Holt et al., Trends Biotech 21(11): 484-490 (2003), Ghahroudi et al., FEBS Lett. 414:521-526 (1997), Lauwereys et al., EMBO J. 17:3512-3520 (1998), Reiter et al., J. Mol. Biol. 290:685-698 (1999), Davies and Riechmann, Biotechnology, 13:475-479 (2001)).

The term "diabodies" refers to small antibody fragments with two antigen-binding sites, which fragments comprise a variable heavy domain ("$V_H$" or "$V_H$") connected to a variable light domain ("$V_L$" or "$V_L$") in the same polypeptide chain ($V_H$-$V_L$). By using a linker that is too short to allow pairing between the two domains on the same chain, the domains are forced to pair with the complementary domains of another chain and create two antigen-binding sites. Diabodies and their production are described more fully in, for example, EP 404,097; WO 93/11161; and Hollinger et al., Proc. Natl. Acad. Sci. USA, 90: 6444-6448 (1993).

The term "parental antibody" means any antibody of interest which is to be mutated or varied to obtain antibodies or fragments thereof which bind to the same epitope as the parental antibody, but with higher affinity.

A "targeting moiety" is the portion of an immunoconjugate intended to target the immunoconjugate to a cell of interest. Typically, the targeting moiety is an antibody, or a fragment of an antibody that retains antigen recognition capability, such as a scFv, a dsFv, an Fab, or an $F(ab')_2$ A "toxic moiety" is the portion of a immunotoxin which renders the immunotoxin cytotoxic to cells of interest. With regard to the immunotoxins which are the subject of the present invention, the toxic moiety is a *Pseudomonas* exotoxin A which has been mutated to reduce its non-specific cytotoxicity, as described in some detail below.

Typically, an immunoglobulin has a heavy and light chain. Each heavy and light chain contains a constant region and a variable region, (the regions are also known as "domains"). Light and heavy chain variable regions contain a "framework" region interrupted by three hypervariable regions, also called "complementarity-determining regions" or "CDRs". The extent of the framework region and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "VH" refer to the variable region of an immunoglobulin heavy chain, including an Fv, scFv, dsFv or Fab. References to "$V_L$" or a "VL" refer to the variable region of an immunoglobulin light chain, including of an Fv, scFv, dsFv or Fab The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond.

The phrase "disulfide stabilized Fv" or "dsFv" refer to the variable region of an immunoglobulin in which there is a disulfide bond between the light chain and the heavy chain. In the context of this invention, the cysteines which form the disulfide bond are within the framework regions of the antibody chains and serve to stabilize the conformation of the antibody. Typically, the antibody is engineered to introduce cysteines in the framework region at positions where the substitution will not interfere with antigen binding.

The term "linker peptide" includes reference to a peptide within an antibody binding fragment (e.g., Fv fragment) which serves to indirectly bond the variable domain of the heavy chain to the variable domain of the light chain.

An antibody immunologically reactive with a particular antigen can be generated by recombinant methods such as selection of libraries of recombinant antibodies in phage or similar vectors, see, e.g., Huse, et al., *Science* 246:1275-1281 (1989); Ward, et al., *Nature* 341:544-546 (1989); and Vaughan, et al., *Nature Biotech.* 14:309-314 (1996), or by immunizing an animal with the antigen or with DNA encoding the antigen.

The term "effector moiety" means the portion of an immunoconjugate intended to have an effect on a cell targeted by the targeting moiety or to identify the presence of the immunoconjugate. In the context of the present invention, the effector moiety is a mutated *Pseudomonas* exotoxin A.

The term "immunoconjugate" includes reference to a covalent linkage of an effector molecule to an antibody.

The terms "effective amount" or "amount effective to" or "therapeutically effective amount" includes reference to a dosage of a therapeutic agent sufficient to produce a desired result, such as inhibiting cell protein synthesis by at least 50%, or killing the cell.

The term "toxin" typically includes reference to abrin, ricin, *Pseudomonas* exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain Ia of PE or the B chain of DT) and replacing it with a different targeting moiety, such as an antibody. In the context of the present invention, the toxin is a mutated *Pseudomonas* exotoxin A.

The term “contacting” includes reference to placement in direct physical association.

An “expression plasmid” comprises a nucleotide sequence encoding a molecule or interest, which is operably linked to a promoter.

As used herein, “polypeptide”, “peptide” and “protein” are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term “residue” or “amino acid residue” or “amino acid” includes reference to an amino acid that is incorporated into a protein, polypeptide, or peptide (collectively “peptide”). The amino acid can be a naturally occurring amino acid and, unless otherwise limited, can encompass known analogs of natural amino acids that can function in a similar manner as naturally occurring amino acids.

The amino acids and analogs referred to herein are described by shorthand designations as follows in Table A:

TABLE A

| Amino Acid Nomenclature | | |
|---|---|---|
| Name | 3-letter | 1-letter |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S-Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A “conservative substitution”, when describing a protein refers to a change in the amino acid composition of the protein that does not substantially alter the protein’s activity. Thus, “conservatively modified variations” of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table B each contain amino acids that are conservative substitutions for one another:

TABLE B

| |
|---|
| 1) Alanine (A), Serine (S), Threonine (T); |
| 2) Aspartic acid (D), Glutamic acid (E); |
| 3) Asparagine (N), Glutamine (Q); |
| 4) Arginine (R), Lysine (K); |
| 5) Isoleucine (I), Leucine (L), Methionine (M), Valine (V); and |
| 6) Phenylalanine (F), Tyrosine (Y), Tryptophan (W). |

See also, Creighton, *Proteins: Structures and Molecular Properties*, W. H. Freeman and Company, New York (2nd Ed., 1992).

The terms “substantially similar” in the context of a peptide indicates that a peptide comprises a sequence with at least 90%, preferably at least 95% sequence identity to the reference sequence over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms “conjugating,” “joining,” “bonding” or “linking” refer to malting two polypeptides into one contiguous polypeptide molecule. In the context of the present invention, the terms include reference to joining an antibody moiety to an effector molecule (EM). The linkage can be either by chemical or recombinant means. Chemical means refers to a reaction between the antibody moiety and the effector molecule such that there is a covalent bond formed between the two molecules to form one molecule.

As used herein, “recombinant” includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, underexpressed or not expressed at all.

As used herein, “nucleic acid” or “nucleic acid sequence” includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolumn* (*Proc. Nat'l Acad. Sci. USA* 82:2306-2309 (1985), or the ciliate Macronucleus, may be used when the nucleic acid is expressed in using the translational machinery of these organisms.

The phrase "fusing in frame" refers to joining two or more nucleic acid sequences which encode polypeptides so that the joined nucleic acid sequence translates into a single chain protein which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli*, or eukaryotic cells such as yeast, insect, amphibian, or mammalian cells.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, more preferably 65%, even more preferably 70%, still more preferably 75%, even more preferably 80%, and most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l, Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "in vivo" includes reference to inside the body of the organism from which the cell was obtained. "Ex vivo" and "in vitro" means outside the body of the organism from which the cell was obtained.

The phrase "malignant cell" or "malignancy" refers to tumors or tumor cells that are invasive and/or able to undergo metastasis, i.e., a cancerous cell.

As used herein, "mammalian cells" includes reference to cells derived from mammals including humans, rats, mice, guinea pigs, chimpanzees, or macaques. The cells may be cultured in vivo or in vitro.

The term "selectively reactive" refers, with respect to an antigen, the preferential association of an antibody, in whole or part, with a cell or tissue bearing that antigen and not to cells or tissues lacking that antigen. It is, of course, recognized that a certain degree of non-specific interaction may occur between a molecule and a non-target cell or tissue. Nevertheless, selective reactivity, may be distinguished as mediated through specific recognition of the antigen. Although selectively reactive antibodies bind antigen, they may do so with low affinity. On the other hand, specific binding results in a much stronger association between the antibody and cells bearing the antigen than between the bound antibody and cells lacking the antigen. Specific binding typically results in greater than 2-fold, preferably greater than 5-fold, more preferably greater than 10-fold and most preferably greater than 100-fold increase in amount of bound antibody (per unit time) to a cell or tissue bearing CD22 as compared to a cell or tissue lacking CD22. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, ANTIBODIES, A LABORATORY MANUAL, Cold Spring Harbor Publications, New York (1988), for a description of immunoassay formats and conditions that can be used to determine specific immunoreactivity.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. Preferably, the immunologically reactive conditions employed in the methods of the present invention are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

*Pseudomonas* Exotoxin

Native *Pseudomonas* exotoxin A ("PE") is an extremely active monomeric protein (molecular weight 66 kD), secreted by *Pseudomonas aeruginosa*, which inhibits protein synthesis in eukaryotic cells. The native PE sequence is set forth in SEQ ID NO:1 of U.S. Pat. No. 5,602,095, incorporated herein by reference. The method of action is inactivation of the ADP-ribosylation of elongation factor 2 (EF-2). The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain Ib (amino acids 365-399) remains undefined, although a large part of it, amino acids 365-380, can be deleted without loss of cytotoxicity. See Siegall, et al., J Biol Chem 264:14256-61 (1989).

The terms "*Pseudomonas* exotoxin" and "PE" as used herein typically refer to a PE that has been modified from the native protein to reduce or to eliminate non-specific toxicity. Numerous such modifications are known in the art and include, but are not limited to, elimination of domain Ia, various amino acid deletions in domains Ib, II and III, single amino acid substitutions and the addition of one or more sequences at the carboxyl terminus such as KDEL (SEQ ID NO:2) and REDL (SEQ ID NO:3). See Siegall, et al., *J. Biol. Chem.* 264:14256-14261 (1989). Cytotoxic fragments of PE include those which are cytotoxic with or without subsequent proteolytic or other processing in the target cell (e.g., as a protein or pre-protein). Cytotoxic fragments of PE include PE40, PE38 and its variants PE38QQR and PE38 KDEL (in which PE38 has the sequence KDEL, SEQ ID NO:2, added at the C-terminus), and PE35, as discussed below. In a preferred embodiment, the cytotoxic fragment of PE retains at least about 20%, preferably at least about 40%, more preferably about 50%, even more preferably 75%, more preferably at least about 90%, and still more preferably 95% of the cytotoxicity of native PE. In particularly preferred embodiments, the cytotoxic fragment has at least the cytotoxicity of native PE, and preferably has more.

In preferred embodiments, the PE has been modified to reduce or eliminate non-specific cell binding, frequently by deleting domain Ia as taught in U.S. Pat. No. 4,892,827, although this can also be achieved, for example, by mutating certain residues of domain Ia. U.S. Pat. No. 5,512,658, for instance, discloses that a mutated PE in which Domain Ia is present but in which the basic residues of domain Ia at positions 57, 246, 247, and 249 are replaced with acidic residues (glutamic acid, or "E")) exhibits greatly diminished non-specific cytotoxicity. This mutant form of PE is sometimes referred to as "PE4E."

PE40 is a truncated derivative of PE previously described in the art. See, Pai, et al., *Proc. Nat'l Acad. Sci. USA* 88:3358-62 (1991); and Kondo, et al., *J. Biol. Chem.* 263:9470-9475 (1988). PE35 is a 35 kD carboxyl-terminal fragment of PE in which amino acid residues 1-279 have deleted and the molecule commences with a met at position 280 followed by amino acids 281-364 and 381-613 of native PE. PE35 and PE40 are disclosed, for example, in U.S. Pat. Nos. 5,602,095 and 4,892,827.

In some preferred embodiments, the cytotoxic fragment PE38 is employed. PE38 contains the translocating and ADP ribosylating domains of PE but not the cell-binding portion (Hwang, J. et al., *Cell*, 48:129-136 (1987)). PE38 is a truncated PE pro-protein composed of amino acids 253-364 and 381-613 which is activated to its cytotoxic form upon processing within a cell (see e.g., U.S. Pat. No. 5,608,039, and Pastan et al., Biochim. Biophys. Acta 1333:C1-C6 (1997)). The sequence of PE38 is therefore known in the art, but could also readily be determined by the practitioner by subtracting the stated residues from the known sequence of PE. Persons of skill will be aware that, due to the degeneracy of the genetic code, the amino acid sequence of PE38, of its variants, such as PE38 KDEL, and of the other PE derivatives discussed herein can be encoded by a great variety of nucleic acid sequences, any of which can be expressed to result in the desired polypeptide.

As noted above, some or all of domain 1b may be deleted, and the remaining portions joined by a linker or directly by a peptide bond. Some of the amino portion of domain II may be deleted. And, the C-terminal end may contain the native sequence of residues 609-613 (REDLK (SEQ ID NO:4)), or may contain a variation found to maintain the ability of the construct to translocate into the cytosol, such as KDEL (SEQ ID NO:2) or REDL (SEQ ID NO:3), and repeats of these sequences. See, e.g., U.S. Pat. Nos. 5,854,044; 5,821,238; and 5,602,095 and WO 99/51643. While in preferred embodiments, the PE is PE4E, PE40, or PE38, any form of PE in which non-specific cytotoxicity has been eliminated or reduced to levels in which significant toxicity to non-targeted cells does not occur can be used in the immunotoxins of the present invention so long as it remains capable of translocation and EF-2 ribosylation in a targeted cell.

In preferred embodiments, the PE molecules are further modified to have a substitution of alanine, glycine, serine or glutamine in place of the amino acid residue normally present at one or more of the positions of the PE molecule set forth in the Introduction, above. Alanine is the most preferred.

A. Conservatively Modified Variants of PE

It is understood that the sequence of native PE and the variants discussed above can have conservative substitutions and retain cytotoxic capability and, desirably, reduced antigenicity compared to the native sequence of PE. In preferred embodiments, modified variants of PE or cytotoxic fragments thereof have at least 80% sequence similarity, preferably at least 85% sequence similarity, more preferably at least 90% sequence similarity, and most preferably at least 95% sequence similarity at the amino acid level, with the PE of interest, such as PE38.

The term "conservatively modified variants" applies to both amino acid and nucleic acid sequences. With respect to particular nucleic acid sequences, conservatively modified variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

B. Assaying for Cytotoxicity or Antigenicity of PE

*Pseudomonas* exotoxins employed in the invention can be assayed for the desired level of cytotoxicity by assays well known to those of skill in the art. Thus, cytotoxic fragments of PE and conservatively modified variants of such fragments can be readily assayed for cytotoxicity. A large number of candidate PE molecules can be assayed simultaneously for cytotoxicity by methods well known in the art. For example, subgroups of the candidate molecules can be assayed for cytotoxicity. Positively reacting subgroups of the candidate molecules can be continually subdivided and reassayed until the desired cytotoxic fragment(s) is identified. Such methods allow rapid screening of large numbers of cytotoxic fragments or conservative variants of PE. Antigenicity can be assayed by, for example, the methods taught in the Examples herein.

Conjugation to the Antibody

In a non-recombinant embodiment of the invention, a targeting molecule, such as an antibody, is linked to a PE molecule of the present invention using any number of means known to those of skill in the art. Both covalent and noncovalent attachment means may be used with PE molecules of the present invention.

The procedure for attaching a PE molecule to an antibody or other targeting molecule ("TM") will vary according to the chemical structure of the TM. Polypeptides typically contain a variety of functional groups; e.g., carboxylic acid (COOH), free amine (—$NH_2$) or sulfhydryl (—SH) groups, which are available for reaction with a suitable functional group on an antibody, for example, to result in the binding of the PE molecule.

Alternatively, the antibody or other TM is derivatized to expose or to attach additional reactive functional groups. The derivatization may involve attachment of any of a number of linker molecules such as those available from Pierce Chemical Company, Rockford Ill.

A "linker", as used herein, is a molecule that is used to join the TM to the PE molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In some circumstances, it is desirable to free the PE molecule from the TM when the immunoconjugate has reached its target site. Therefore, in these circumstances, immunoconjugates will comprise linkages which are cleavable in the vicinity of the target site. Cleavage of the linker to release the PE molecule from the TM may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

Production of Immunoconjugates

Immunoconjugates of the invention include, but are not limited to, molecules in which there is a covalent linkage of a PE molecule to an antibody or other targeting agent. The choice of a particular targeting agent depends on the particular cell to be targeted. With the PE molecules provided herein, one of skill can readily construct a variety of clones containing functionally equivalent nucleic acids, such as nucleic acids which differ in sequence but which encode the same PE and antibody sequence. Thus, the present invention provides nucleic acids encoding antibodies and PE conjugates and fusion proteins thereof.

A. Recombinant Methods

The nucleic acid sequences of the present invention can be prepared by any suitable method including, for example, cloning of appropriate sequences or by direct chemical synthesis by methods such as the phosphotriester method of Narang, et al., *Meth. Enzymol.* 68:90-99 (1979); the phosphodiester method of Brown, et al., *Meth. Enzymol.* 68:109-151 (1979); the diethylphosphoramidite method of Beaucage, et al., *Tetra. Lett.* 22:1859-1862 (1981); the solid phase phosphoramidite triester method described by Beaucage & Caruthers, *Tetra. Letts.* 22(20):1859-1862 (1981), e.g., using an automated synthesizer as described in, for example, Needham-VanDevanter, et al. *Nucl. Acids Res.* 12:6159-6168 (1984); and, the solid support method of U.S. Pat. No. 4,458, 066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the nucleic acid sequences of this invention are prepared by cloning techniques. Examples of appropriate cloning and sequencing techniques, and instructions sufficient to direct persons of skill through many cloning exercises are found in Sambrook, et al., MOLECULAR CLONING: A LABORATORY MANUAL (2ND ED.), Vols. 1-3, Cold Spring Harbor Laboratory (1989)), Berger and Kimmel (eds.), GUIDE TO MOLECULAR CLONING TECHNIQUES, Academic Press, Inc., San Diego Calif. (1987)), or Ausubel, et al. (eds.), CURRENT PROTOCOLS IN MOLECULAR BIOLOGY, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Nucleic acids encoding native PE can also be modified to form the immunoconjugates of the present invention. Modification by site-directed mutagenesis is well known in the art. Nucleic acids encoding PE can be amplified by in vitro methods. Amplification methods include the polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In a preferred embodiment, immunoconjugates are prepared by inserting the cDNA which encodes an antibody or other TM of choice into a vector which comprises the cDNA encoding a desired PE of the invention. The insertion is made so that the targeting agent (for ease of discussion, the discussion herein will assume the targeting agent is an Fv, although other targeting agents could be substituted with equal effect) and the PE are read in frame, that is in one continuous polypeptide which contains a functional Fv region and a functional PE region. In a particularly preferred embodiment, cDNA encoding a PE of the invention is ligated to a scFv so that the toxin is located at the carboxyl terminus of the scFv. In other preferred embodiments, cDNA encoding a PE of the invention is ligated to a scFv so that the toxin is located at the amino terminus of the scFv.

Once the nucleic acids encoding a PE, antibody, or an immunoconjugate of the present invention are isolated and cloned, one may express the desired protein in a recombinantly engineered cell such as bacteria, plant, yeast, insect and mammalian cells. It is expected that those of skill in the art are knowledgeable in the numerous expression systems available for expression of proteins including *E. coli*, other bacterial hosts, yeast, and various higher eucaryotic cells such as the COS, CHO, HeLa and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli* this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

One of skill would recognize that modifications can be made to a nucleic acid encoding a polypeptide of the present invention (i.e., PE or an immunoconjugate formed from a PE of the invention) without diminishing its biological activity. Some modifications may be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly H is) to aid in purification steps.

In addition to recombinant methods, the immunoconjugates and PEs of the present invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3-284; Merrifield, et al. *J. Am. Chem. Soc.* 85:2149-2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are known to those of skill.

B. Purification

Once expressed, the recombinant immunoconjugates and PEs of the present invention can be purified according to standard procedures of the art, including ammonium sulfate precipitation, affinity columns, column chromatography, and the like (see, generally, R. Scopes, PROTEIN PURIFICATION, Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies of this invention. See, Buchner, et al., *Anal. Biochem.* 205:263-270 (1992); Pluckthun, *Biotechnology* 9:545 (1991); Huse, et al., *Science* 246:1275 (1989) and Ward, et al., *Nature* 341:544 (1989), all incorporated by reference herein.

Often, functional heterologous proteins from *E. coli* or other bacteria are isolated from inclusion bodies and require solubilization using strong denaturants, and subsequent refolding. During the solubilization step, as is well-known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena, et al., *Biochemistry* 9: 5015-5021 (1970), incorporated by reference herein, and especially as described by Buchner, et al., supra.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione, and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

Pharmaceutical Compositions and Administration

The immunoconjugate compositions of this invention (i.e., PE linked to an antibody) are particularly useful for parenteral administration, such as intravenous administration or administration into a body cavity.

The compositions for administration will commonly comprise a solution of the antibody and/or immunoconjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical immunotoxin composition of the present invention for intravenous administration would be about 0.1 to 10 mg per patient per day. Dosages from 0.1 up to about 100 mg per patient per day may be used. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the immunoconjugate compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp. 315-339, (1992) both of which are incorporated herein by reference.

Polymers can be used for ion-controlled release of immunoconjugate compositions of the present invention. Various degradable and nondegradable polymeric matrices for use in controlled drug delivery are known in the art (Langer, R., *Accounts Chem. Res.* 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston, et al., *Pharm. Res.* 9:425-434 (1992); and Pec, et al., *J. Parent. Sci. Tech.* 44(2):58-65 (1990)). Alternatively, hydroxyapatite has been used as a microcarrier for controlled release of proteins (Ijntema, et al., *Int. J. Pharm.* 112:215-224 (1994)). In yet another aspect, liposomes are used for controlled release as well as drug targeting of the lipid-capsulated drug (Betageri, et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Among various uses of the immunotoxins of the present invention are included a variety of disease conditions caused by specific human cells that may be eliminated by the toxic action of the fusion protein.

In Vitro Uses

In another embodiment, this invention provides for kits for eliminating target cells in vitro or ex vivo using PEs of the invention. For example, immunotoxins comprising a PE of the invention can be used to purge targeted cells from a population of cells in a culture. Thus, for example, cells cultured from a patient having a cancer expressing CD22 can be purged of cancer cells by contacting the culture with immunotoxins which use anti-CD22 antibodies as a targeting moiety.

In some instances, the target cells may be contained within a biological sample. A "biological sample" as used herein is a sample of biological tissue or fluid that contains target cells and non-target cells. Such samples include, but are not limited to, tissue from biopsy, blood, and blood cells (e.g., white cells). A biological sample is typically obtained from a multicellular eukaryote, preferably a mammal such as rat, mouse, cow, dog, guinea pig, or rabbit, and more preferably a primate, such as a macaque, chimpanzee, or human. Most preferably, the sample is from a human.

EXAMPLES

Example 1

This Example sets forth the experimental procedures used in, and the results of, the studies reflected in FIG. 1.

Experimental Procedure

Immune complex capture ("ICC")-ELISA: ICC ELISA detects Ag-Ab reactions in solution. Microtiter plates were coated with 2 µg/ml of CD25-rabbit Fc (human CD25 alpha extra-cellular domain fused to the Fc of rabbit IgG1) or with CD22-hFc human CD22 extracellular domain fused to the Fc of human IgG1) in phosphate buffered saline (PBS) for overnight at 4° C. In a separate tube, Ab samples were serially diluted in blocking buffer, and mixed with 2 µg/ml of anti-CD22 or anti-CD25 immunotoxin. The plates were washed, and then, the immunotoxin-Ab mixtures were transferred individual wells. The plates were incubated more than 1 hr at room temperature ("RT"). The immune complexes captured on wells were detected by horserasdish peroxidase ("HRP")-conjugated goat anti-mouse IgG. After incubation for 1 hr at RT, the plates were washed, and tetramethylbenzidine ("TMB") substrate was added. After 10 min, 1M sulfuric acid was added. The absorbance was measured at 450 µm with 600 nm as a reference.

Direct coating ("DC")-ELISA: DC-ELISA does not detect antibodies against conformational epitopes that are destroyed by adsorption to the plate but can detect non-conformational epitopes. Microtiter plates were coated with 2 µg/ml of immunotoxin in PBS overnight at 4° C. After washing, serial diluted Ab in blocking buffer was added and incubated overnight at 4° C. The detection step used the same secondary antibodies as the ICC-ELISA.

Serum samples: Patients with B cell malignancies (BL1, BL2, and BL3) received BL22 intravenously on days 1, 3, and 5 as part of a phase I clinical trial conducted at the National Cancer Institute. After 3 treatment cycles, serum samples were obtained. Antibody titers against PE38 were determined by ICC and by DC ELISA. These three patients' sera had over 75% neutralization activity based on the neutralizing criteria for the phase I clinical trial. Patients with mesothelioma ("Meso 1", and "Meso 2") received immunotoxin SS1P. Serum was obtained after 1 cycle of treatment. ICC and DC ELISA and neutralization assays were done. Patient with epithelial cancer received LMB-9. After 1 cycle, serum was obtained. ICC and DC ELISA and neutralization assays were done.

Representative data of antibody responses in patients treated with three different immunotoxins, BL22, SSLP and LMB9 are shown in FIG. 1. BL22, SSLP, LMB9 and LMB2 are the names of specific immunotoxins known in the art, each of which uses PE38 as the toxic portion and which use as the targeting portion an antibody Fv region, as follows: (i) for BL22, an anti-CD22 Fv, (ii) for SS1P, an anti-mesothelin Fv, (iii) for LMB9, an anti Lewis Y Fv, and (iv) for LMB2, an anti CD25 Fv. Each of these immunotoxins is or has been the subject of a clinical trial. Serum samples were collected from each patient and tested for their neutralizing activity (based on the criteria of the clinical trials) in a cell killing assay (FIG. 1, bar graphs) and their reactivity with immunotoxins in different ELISAs (FIG. 1, line graphs). The immunotoxin used for the treatment and the type of patient are listed in the top of the FIG. 1 panels. The numbers of cycles of treatment that the patient had been given before serum collection and the days after the last treatment cycle are shown in the FIG. 1 line graph panels. The samples were chosen from the patients who generated neutralizing antibodies so that they could not receive further treatment (>75% neutralization of immunotoxins). The neutralization was assessed not only with the immunotoxin used for the treatment but also with different immunotoxins with different Fvs. The immunotoxin used for the neutralization assay is indicated in each bar.

Very similar neutralization activities were observed using the two different immunotoxins (seen in BL1 and BL2 cases) indicating that the neutralizing activity is mainly due to antibody which recognizes PE38.

The FIG. 1 line graphs show the antibody in the serum samples measured by 2 different ELISAs. The diamond symbols show ICC-ELISA signals. ICC-ELISA can measure antibodies reacting with the native form of PE38. The circles show the results using DC-ELISAs. In all cases, the ICC-ELISA gave stronger signals than the DC-ELISA, indicating that antibodies to native PE38 were the dominant type generated in the patients. Patients treated with different immunotoxins and with different cancers showed similar antibody responses in these assays.

Example 2

Experimental Procedure

MAbs against PE38 were produced by a standard fusion protocol. Balb/c, A/J, C3H strains of mice were immunized 4-5 times by injection of 4-10 µg of various ITs at 2 weeks intervals. Four weeks after the final injection, the mice were boosted with 4 µg IT and 4 days later the fusion carried out. Spleen cells were isolated and fused with SP2/0 myeloma cells. After selection in hypoxanthine/aminopterine/thymidine medium, the supernatants were screened for specific antibody production with ICC ELISA and/or a neutralization assay and/or ELISA with microtiter plates coated with a 1 mg/ml solution of ITs in PBS. The bound immunoglobulins were detected with horseradish peroxidase-conjugated mouse anti-kappa IgG or goat anti-mouse IgG (Jackson). Positive clones were used for the production of antibodies in culture supernatants.

Immunization Strategy

To obtain monoclonal antibodies that react with conformational epitopes on the native structure of the immunotoxin, we immunized mice with various immunotoxins containing PE38 and saved those hybridomas that only reacted with PE38 using the indirect ELISA. To obtain a diffuse set of antibodies we immunized 3 strains of mice (Balb/c, A/J and C3H Hej) using several different immunotoxins. We began our immunizations with anti-Tac(dsFv)-PE38, and found that the hybridoma yield was low even though the serum titers were high. We assumed the immunotoxin was somehow damaging spleen cells and giving low hybridoma yields. To avoid possible killing of the specific B-cells via surface IgG we also immunized mice with mutant forms of the immunotoxin that had very low cytotoxic activity due to point mutations at positions 553 (E to D) or 276 (R to G). These mutations are located at different sites on the surface of PE38. Therefore all possible epitopes on PE38 should be present in at least one of the mutants.

A total of 16 fusions involving 22 immunized mice were performed. We retained 60 hybridomas that showed high titers in the ICC ELISA. Table 2, below, shows a comparison of the titers of these MAbs in DC-ELISA and in ICC-ELISA. All MAbs showed a higher titer in ICC-ELISA than in the DC-ELISA, indicating that the MAb panel predominantly represents the patients' antibody response detected in the ICC-ELISA.

All antibodies were of the IgG1 isotype except for one IgG2a (IP16) and three IgG2b (IP36, IP37 and IP49). The affinity of each MAb was determined by Biacore in which the MAb was captured on a chip by a rabbit anti-mouse antibody and the BL22 immunotoxin flowed over the chip (Canziani et al., "Kinetic screening of antibodies from crude hybridoma samples using Biacore," Anal. Biochem. 325:301-307 (2004)). The Kds are shown and ranged from 0.0004 to 81 nM.

Example 3

Figure 2:

This Example sets forth the experimental procedures used in, and the results of, the studies reflected in FIG. 2.

Experimental Procedure

Mutual competition of all possible pairs of anti-PE38 MAbs was examined as previously described (Nagata et al., "Rapid grouping of monoclonal antibodies based on their topographical epitopes by a label-free competitive immunoassay," J. Immunol. Methods 292:141-155 (2004)). Microtiter plates (MaxiSoap, Nalge Nunc, Rochester, N.Y.) were coated with 200 ng/50 µg/well of goat anti-mouse IgG (Jackson Immuno Research, Grove, Pa.) in PBS overnight at 4° C. After washing 2 µg/ml of indicator MAb #1 (culture supernatant of hybridoma culture) was added to each well and incubated overnight at 4° C. In a separate tube, competitor MAb #2 was diluted (6 µg/ml) in blocking buffer and mixed with 10 ng/ml of anti-CD30 IT, T6 and incubated overnight at 4° C. The plates were washed twice, and then the MAb #2 IT mixture was transferred to each well (50 µg/ml). For standards, dilutions of the antigens in blocking buffer (1-10 ng/ml for IT) were placed in the same plate. The plates were incubated for 1 hr at RT and washed twice. The immune complexes captured on plates were probed by 50 µl/well of HRP-conjugated goat anti-human IgG (Jackson). After incubation for 2 hr at RT, plates were washed and tetramethylbenzidine substrate (TMB substrate kit, Pierce, 100 µl/well) was added. After 10-20 min, the enzyme reaction was stopped by adding 50 µl/well of 2 N sulfuric acid. The absorbance was measured at 450 nm with 600 nm as a reference.

Example 4

Topographical Epitope Mapping

Using the above method, we carried out topographical epitope mapping based on mutual competition of all possible pairs of antibodies. This method not only identifies antibodies binding to the same epitope but also provides quantitative data on the strength of their interactions. This data is shown in FIG. 2, using a color code in which red represents a very strong competition and light blue no competition.

The data shows that there are 7 major epitope groups and using a stability index of clustering these can be further divided into 13 subgroups. The epitope groups are clearly discrete with relatively little overlap indicating that there are a limited number of epitopes on the PE38 molecule that are very immunogenic.

Figure 3:
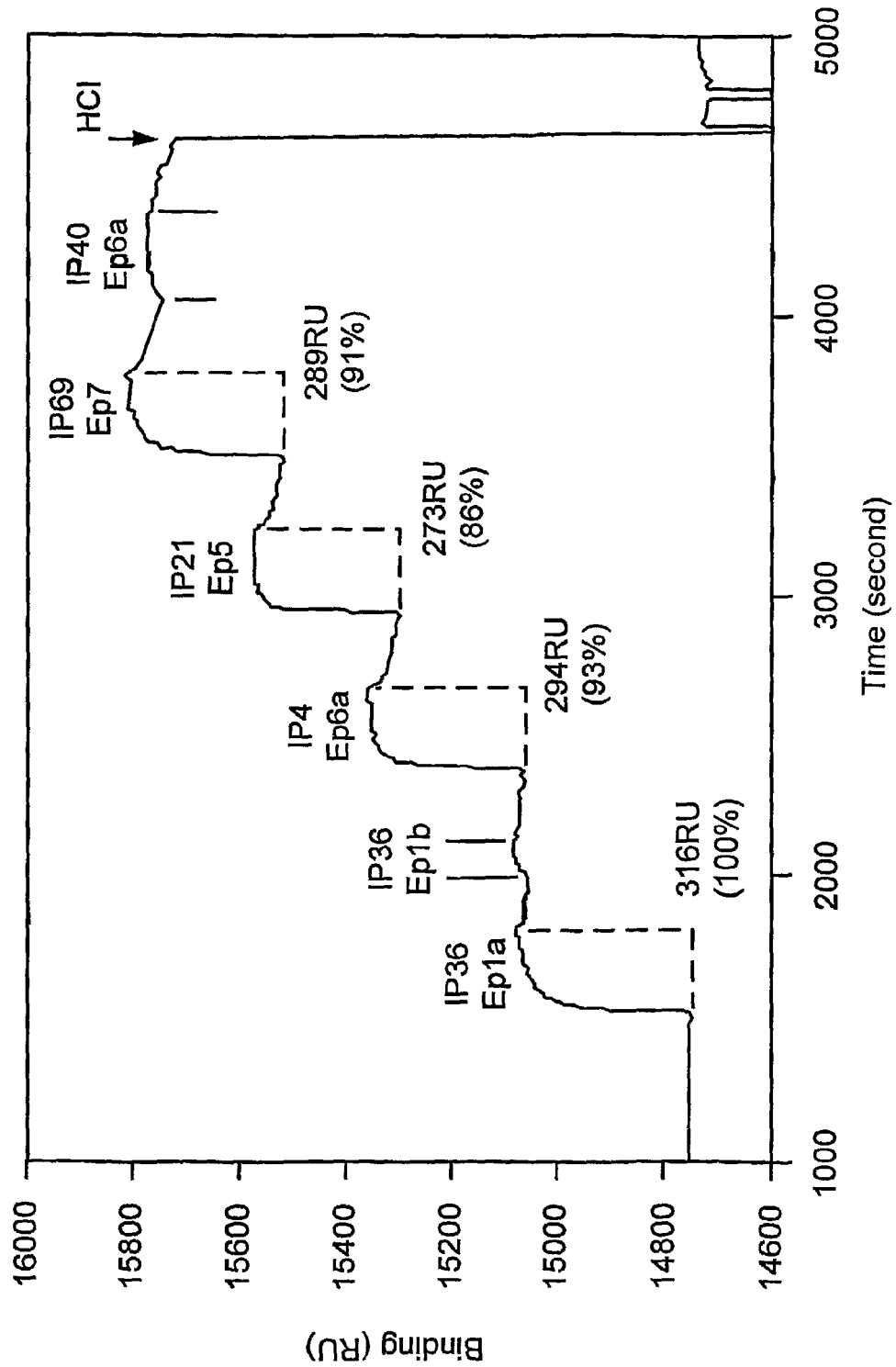

This Example sets forth the procedures used in, and the results of, the studies whose results are reported in FIG. 3.

To confirm that there are a limited number of epitopes on PE38, we used Biacore. M1 immunotoxin was diluted to 50 µg/ml in amine coupling buffer and immobilized to a BIAcore sensor chip CM5 (Laricchia et al., "Epitope mapping analysis of apolipoprotein B-100 using a surface plasmon resonance-based biosensor," Biosens. Bioelectron. 16:963-969 (2001)). Each MAb was purified with protein G Sepharose™, diluted to 50 µg/ml in PBS and injected over the chip surface at 10 µl/min. The MAbs reacting with different epitopes additively bound to the PE38 on the chip but MAbs assigned to the same epitope group did not increase the signal because the epitope was already occupied by pre-bound MAb. In different experiments, MAbs at 50 µg/ml (~=500 nM) were shown to be enough to saturate the binding sites. Also the level of binding of a mixture of IP36, IP4, IP21 and IP69 is the almost the same as the accumulated binding level achieved by the sequential injections.

This data confirm that the epitopes identified in FIG. 2 are non-overlapping epitopes. At least 4 different antibodies can bind to the PE38 molecule at the same time.

Example 5

This Example sets forth the procedure used in the studies identifying the location of epitopes of PE38. The results of the studies are set forth in FIG. 4.

Experimental Procedure
Competition ELISA to Determine the Binding of MAbs to a Series of Mutants of PE38

The competitive effect of each mutant immunotoxin on the binding of each MAb to immunotoxin containing wild type PE38 was measured in an ELISA. Microtiter plates were coated with 3 µg/ml of mesothelin-rFc (the Fc of rabbit IgG1 fused to the human mesothelin extracellular domain) in PBS overnight at 4° C. After washing, 2 µg/ml of SS1P in blocking buffer was added to each well and incubated overnight at 4° C. In separate tubes, a series of 4-fold dilutions of each mutant (0.04-10000 ng/ml) was mixed with each MAb at 4° C. overnight to reach equilibrium. The concentration of each MAb in the mixtures had been pre-determined in separate ELISAs without the competitors as the values to give half maximum signals in the ELISA. The uncomplexed MAb in the mixtures was then captured by SS1P immunotoxin (an anti-mesothelin dsFv fused to wild type PE38) that had been coated on the plate via a mesothelin-Fc fusion protein. A mutant immunotoxin possesses a different Fv and can not be trapped by the mesothelin-Fc on the plates. The free MAb level trapped by SS1P was dependent on the cross reactivity of the MAb to the mutant and on the concentration of the mutant. Finally the amount of MAb associated with the SS1P was measured by the incubation with HRP-labeled goat anti-mouse IgG (H+L) followed by TMB substrate.

Location of Epitopes

We had previously made a number of mutations in PE38 to obtain information about the function of these residues and showed it was possible to modify many residues without loss of function. We used these mutants and new ones in which we intentionally mutated surface residues with long hydrophilic side chains to alanine, glycine, or glutamine and used these to locate the position of the epitopes using a competitive binding assay. The results was evaluated as cross reactivity to the wild type immunotoxin, which was defined as the ratio of concentrations of each mutant and of the wild type that were required for the binding to the same amount of each MAb (Miller J J, Valdes R. "Methods for calculating Cross-reactivity in immunoassays" J. Clin. Immunoassay, 15:97-107 (1992)) This assay not only measures binding but also how much the binding is decreased by the mutation. The data in FIG. 4 shows the results using 45 different point mutants. About half of the mutations result in a decrease of binding of some of the antibodies. There are several interesting features. One is that single point mutations often decrease the binding of all the antibodies in that epitope group. A second is that more than one mutation can decrease the binding of antibodies in a particular epitope group.

Example 6

This Example discusses the results of the studies discussed above.

We defined an epitope-related amino acid as one whose replacement with alanine or glycine decreased at least 20-fold the binding to more than two MAbs assigned for the same epitope. Based on this criterion, N314, E327, E331 and Q332 were identified as Ep1-related amino acids. In the same way, P290, R467 and R538, D313, N314 and D324, R432, E431 and R505, R490 and R576, R513 and E548 and K590 were respectively identified as Ep2b, 2c, 3, 4a, 5, 6a, and 7-related amino acids. We found that mutations that affected MAb binding could be established for 10 of the 13 epitope subgroups. Three subgroups could not be identified. This was due either to not having enough Mabs to study or because no mutant showed a loss of binding.

These data indicate that we can change the antigenicity of PE38 by introducing mutations that destroy the epitope. Immunotoxins with these mutations are expected to be less immunogenic.

Example 7

This Example sets forth the procedures used for the construction, production, and purification of immunotoxins used in the studies reported herein.

The mutated immunotoxins listed in Table 3 were produced by standard protocol as described previously (Pastan et al., "Recombinant immunotoxins in the treatment of cancer," Methods Mol. Biol., 248:503-518 (2004)). Most of the mutations were made in immunotoxin HA22 (Salvatore et al, "Improved cytotoxic activity towards cell lines and fresh leukemia cells of a mutant anti-CD22 immunotoxin obtained by antibody phage display", Clin. Cancer Res., 8:995-1002 (2002)), but some were made in immunotoxin M1(dsFv)-PE38. Mutations were made by Kunkel's method with minor modifications. The component of ITs were expressed in *Escherichia coli* BL21(lambda DE3) and accumulated in inclusion bodies. Inclusion bodies were solubilized and refolded by dilution in a refolding buffer. Active monomeric protein was purified from the refolding solution by ion exchange and size exclusion chromatography to near homogeneity as previously described. Protein concentrations were determined by Bradford assay (Coomassie Plus, Pierce, Rockford, Ill.).

Cytotoxicity Assay

Using Daudi cells, the activity of the ITs was assessed by a protein synthesis inhibition assay (inhibition of incorporation of tritium-labeled leucine into cellular protein) in 96 well plates as described previously (Kreitman et al., "Complete regression of human B-cell lymphoma xenografts in mice treated with recombinant anti-CD22 immunotoxin RFB4 (dsFv)PE38 at doses tolerated by cynomolgus monkeys," Int. J. Cancer, 81:148 (1999)). The activity of the molecule is defined by the $IC_{50}$, the toxin concentration that reduced incorporation of radioactivity by 50% compared with cells that were not treated with toxin. The relative activity was calculated using wild type PE38 immunotoxins as standard. Most mutants retain good cell killing activity. (Salvatore G. et al., "Improved cytotoxic activity towards cell lines and fresh leukemia cells of a mutant anti-CD22 immunotoxin obtained by antibody phage display," Clin. Cancer Res., 8:995-1002 (2002)).

Example 8

This Example discusses the locations of the epitope-related mutations on the PE38 structure.

A PE38 model was constructed by the extraction of the PE38-corresponding residues from a *Pseudomonas* exotoxin A crystal structure (Wedekind J E et al. "Refined crystallographic structure of *Pseudomonas aeruginosa* exotoxin A and its implications for the molecular mechanism of toxicity,"

J. Mol. Biol. 314: 823-837 (2001)). All the mutated amino acids were located. If more than two MAbs assigned to the same epitope had a decrease in binding to a mutant, the mutated residue was identified as an epitope-related amino acid (the binding experiments shown in FIG. 4).

Example 9

A series of cytotoxicity assays were performed on immunotoxins made with PE38 in which single or multiple mutations of various residues were made in the sequence of PE. For ease of comparison, all the immunotoxins used the same targeting moiety. The results of the studies are set forth in Table 4. The first column starts with "HA22," which is an immunotoxin constructed of an anti-CD22 antibody fused to PE38 (see, e.g., Salvatore et al., Clin. Cancer Res. 8(4):995-1002 (2002)). Each designation in column 1 below "HA22" identifies an immunotoxin which is identical to HA22, except for the substitution of one or more residues of the PE38 moiety. The residues or residues which have been mutated are identified by stating in single letter code the residue normally present at the position identified by the number, the number of the position, and on the right side of the number, the residue introduced at the stated position (thus, for example, "Q332A" indicates that the glutamine normally found at position 332 of the native 613 amino acid sequence of PE (SEQ ID NO.:1) was mutated to alanine, while R467A indicates that the arginine normally found at the position corresponding to position 467 of SEQ ID NO.:1 was mutated to alanine, and so on). The second column identifies the epitope or epitopes of PE which the mutation or combination of mutations affects by reducing immunogenicity. The third column, entitled "# of Mabs in this epitope group" identifies how many monoclonal antibodies ("Mabs") have been identified which bind to that epitope. The next 14 columns show the results of cytotoxicity assays conducted on the various immunotoxins. Since the assays were performed at different times, using several different cell types, comparisons between the cytotoxicity of various immunotoxins can only be made between figures in the same column. The numbers shown in these columns are the $IC_{50}$s of the immunotoxins, stated in ng/ml.

Figure 5:
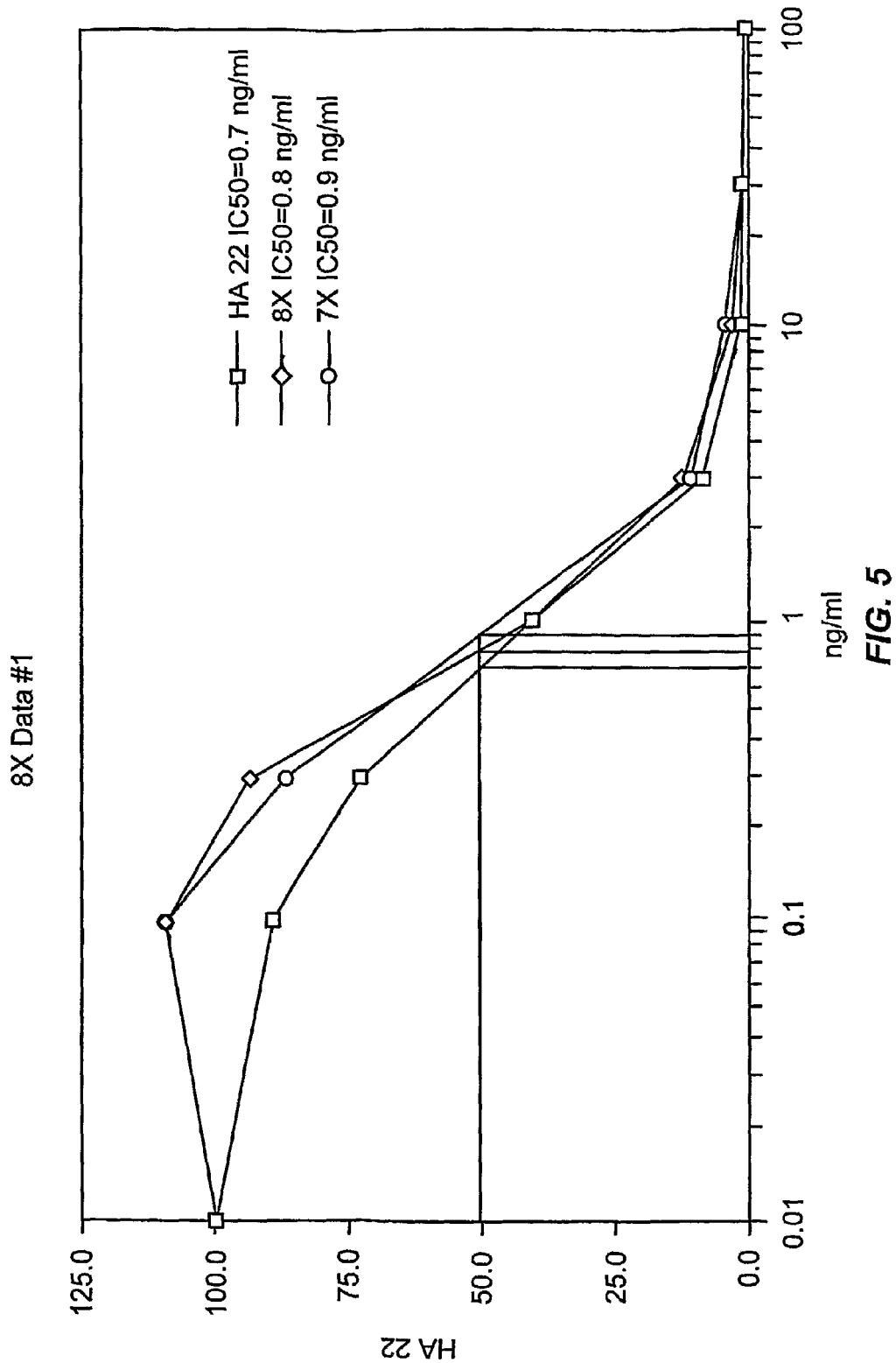

Table 4 further shows a series of combinations of successive mutations, in which first 4, then five, then six, then seven and, finally, eight residues were mutated. The particular residues were selected for mutation since each destroys a different epitope of PE. FIG. 5 shows that the $IC_{50}$ of the mutant in which seven mutations were combined (the "7×" mutant) and the $IC_{50}$ of the mutant in which eight mutations were combined (the "8×" mutant), were close to that of the starting immunotoxin, HA22. The 7× mutant has the following substitutions for the amino acid residues corresponding to the designated residues of SEQ ID NO.:1: R313A, Q332S, R432G, R467A, R490A, R513A, and K590S, while the 8× mutant has all of these mutations, plus a mutation of E548S. Since the mutations selected were previously shown to destroy the ability of antibodies to particular epitopes to recognize those epitopes, it is expected that the combination mutants will exhibit sharply reduced immunogenicity compared to PE38 and other currently used PE variants.

Example 10

Figure 6:
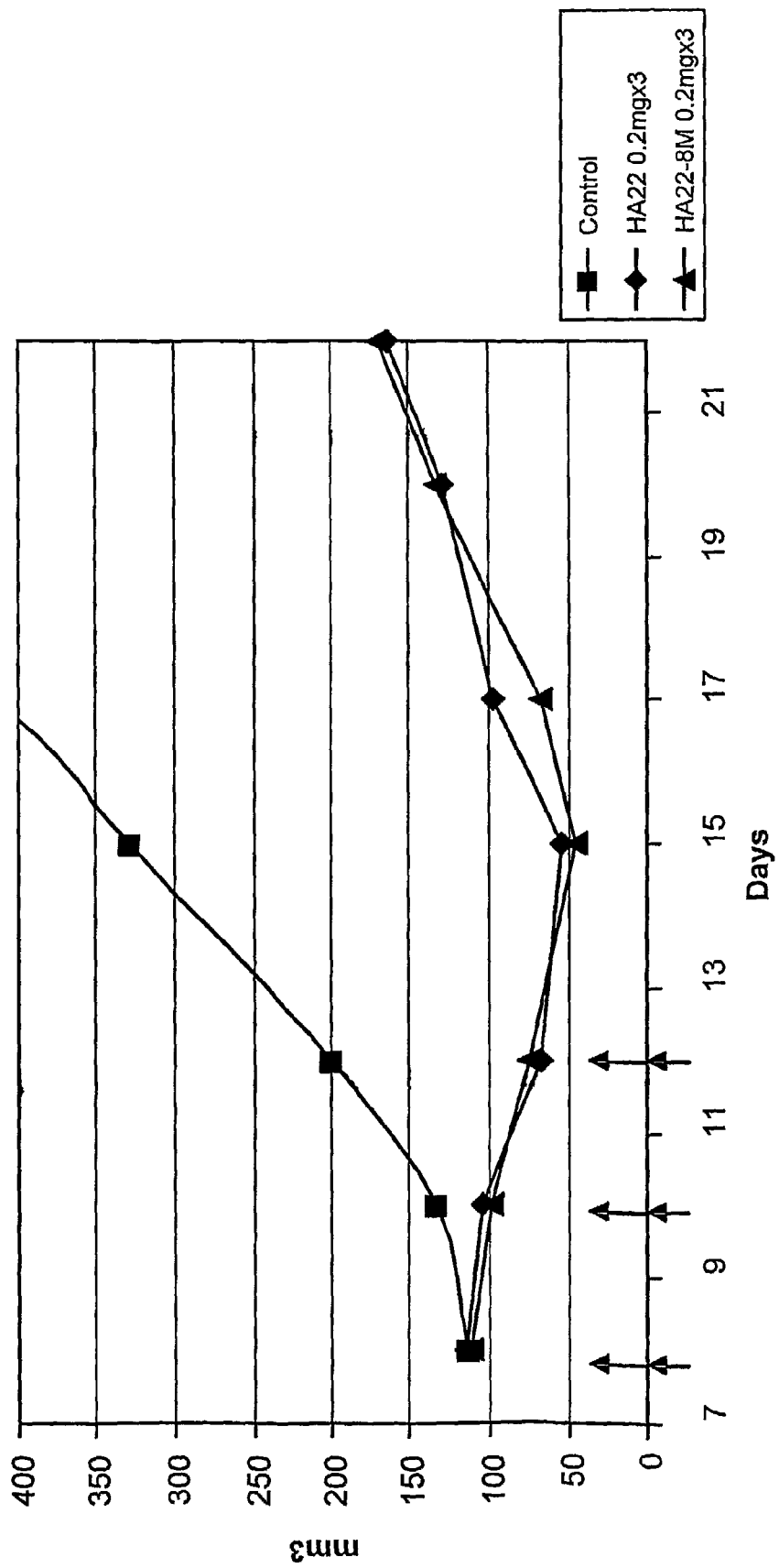

FIG. 6 shows the results of in vivo tests of the effect of the 8× mutant on a human tumor in a mouse xenograft model. "CA46" is a lymphoma that grows subcutaneously as a solid tumor in mice. The tumor cells were introduced into the mice on day 0. The mice were divided into groups, which received either vehicle (control) or one of two immunotoxins on days 8, 10 and 12. The immunotoxins were HA22, an anti-CD22 immunotoxin which uses PE38 as the toxic moiety, and the 8× mutant, which is the same anti-CD22 antibody, fused to PE38 which has the following substitutions for the amino acid residues corresponding to the designated residues of SEQ ID NO.:1: R313A, Q332S, R432G, R467A, R490A, R513A, E548S, and K590S. FIG. 6 shows that the 8× mutant had cytotoxicity to the CA46 tumor similar to that of the starting immunotoxin. Thus, the PEs of the invention can be substituted as the cytotoxic moiety of immunotoxins. Given the epitope mapping shown in FIG. 4, it is further expected that these immunotoxins will have sharply lower immunogenicity than immunotoxins made with currently available PEs.

TABLE 1

Summary of production of anti-PE38 MAbs

| Fusion | Immunization | Final Booster | Mouse | Titer M1-coated ELISA | Titer CD30-ICC-ELISA | Screening Method | Number of final clones (c) |
|---|---|---|---|---|---|---|---|
| 1 | M1-iv × 2 + M1-ip × 3 | M1-ip | Balb/c, pool of 2 mice | $10^5$ | | M1 coated | 2 |
| 2 | M1-iv × 2 + M1-ip × 3 | M1-iv | Balb/c, pool of 2 mice | $10^5$ | | M1 coated | 0 |
| 3 | M1-iv × 2 + M1-ip × 3 | M1-ip | Balb/c, pool of 2 mice | $10^5$ | | M1 coated + M1-biotin | 0 |
| 4 | M1-iv × 2 + M1-ip × 3 | M1-ip | Balb/c, pool of 2 mice | $10^5$ | | M1 coated + M1-biotin + CD30-ICC | 5 |
| 5 | M1-iv × 2 + M1-ip × 3 | M1-ip | Balb/c, pool of 2 mice | $10^5$ | | M1 coated + M1-biotin | 0 |
| 6 | M1-ip × 3 | M1-ip | Balb/c, pool of 2 mice | $5 \times 10^4$ | | M1 coated + M1-biotin + CD30-ICC | 0 |
| 7 | M1-ip × 6+ | D553E-ip | Balb/c | $10^5$ | | M1 coated + CD30-ICC | 3 |
| 8 | M1-ip × 4 | D553E-ip | Balb/c | $5 \times 10^4$ | | M1 coated + CD30-ICC | 21 |
| 9 | D553E-ip × 4 | D553E-ip | A/J | $3 \times 10^3$ | $10^5$ | M1 coated + CD30-ICC + Neutralization | 31 |

TABLE 1-continued

Summary of production of anti-PE38 MAbs

| Fusion | Immunization | Final Booster | Mouse | Titer M1-coated ELISA | Titer CD30-ICC-ELISA | Screening Method | Number of final clones (c) |
|---|---|---|---|---|---|---|---|
| 10 | R276G-ip × 4 | R276G-ip | A/J | 10 4 | $10^5$ | M1 coated + CD30-ICC + Neutralization | 7 |
| 11 | R276G-ip × 5 | R276G-ip | A/J | | 10 4 | M1 coated + CD30-ICC + Neutralization | 1 |
| 12 | R276G-ip × 6 | R276G-ip | Balb/c | | 10 4 | M1 coated + CD30-ICC + Neutralization | 16 |
| 13 | D553E-ip × 7 | D553E-ip | Balb/c | | $10^5$ | CD30-ICC | 7 |
| 14 | M1-ip × 4 | D553E-ip | C3H Hej | | $3 \times 10^4$ | CD30-ICC | 0 |
| 15 | M1-ip × 3 + D553E × 2 | III-ip | A/J | | $3 \times 10^5$ | CD30-ICC | 3 |
| 16 | M1-ip × 3 + D553E × 2 | D553E-ip | A/J | | $3 \times 10^5$ | CD30-ICC | 13 |

(c) Clones are selected by their relatively high affinity in ICC-ELISA using M40-3 as the standard.
M1: M1(dsFv)-PE38,
D553E: LMB-2 mutant with D553E,
R276G: M1(scFv)PE38 mutant with R276G,
III: domain III

TABLE 2

List of Mabs Studied

| Name | Epitope | Isotype | Titer (Log μl/μg) | Affinity (nM) |
|---|---|---|---|---|
| IP43 | 1a | γ/1 | 2.6 | 0.10 |
| IP62 | 1a | γ/1 | 2.5 | 0.2 |
| IP57 | 1a | γ/1 | 1.9 | 0.00039 |
| IP11 | 1b | γ/1 | 2.6 | 6* |
| IP39 | 1b | γ/1 | 2.8 | 0.93* |
| IP47 | 1b | γ/1 | 2.8 | 0.47* |
| IP70 | 1b | γ/1 | 2.5 | 58* |
| IP48 | 1b | γ/1 | 2.7 | 3.3* |
| IP1 | 1b | γ/1 | 2.6 | 5.80 |
| IP35 | 1b | γ/1 | 2.8 | 3.70 |
| IP36 | 1b | γ/1 | 2.6 | 3.60 |
| IP42 | 1b | γ/1 | 2.5 | 43 |
| IP34 | 2a | γ/1 | 2.7 | 0.11* |
| IP29 | 2b | γ/1 | 2.8 | 20 |
| IP63 | 2b | γ/1 | 2.7 | 5 |
| IP2 | 2b | γ/1 | 2.7 | 0.30 |
| IP15 | 2c | γ/1 | 2.6 | 5.3 |
| IP22 | 2c | γ/1 | 2.6 | 3.4* |
| IP51 | 2c | γ/1 | 2.2 | 3.10 |
| IP76 | 2c | γ/1 | 3.0 | 0.19 |
| IP83 | 2c | γ/1 | 2.5 | 0.43 |
| IP9 | 3a | γ/1 | 2.4 | 4.80 |
| IP18 | 3a | γ/1 | 2.5 | 0.09* |
| IP16 | 3a | γ/1 | 2.5 | 0.24* |
| IP32 | 3a | γ/1 | 2.7 | 33 |
| IP44 | 3b | γ/1 | 2.5 | 0.14 |
| IP45 | 3b | γ/1 | 2.9 | 0.47 |
| IP58 | 3b | γ/1 | 2.4 | 0.24 |
| IP7 | 4a | γ/1 | 2.7 | 0.04 |
| IP10 | 4a | γ/1 | 2.1 | 0.04 |
| IP31 | 4a | γ/1 | 2.9 | 0.27* |
| IP37 | 4a | γ/1 | 2.7 | 1.40 |
| IP49 | 4a | γ/1 | 1.7 | 2.60 |
| IP3 | 4a | γ/1 | 2.6 | 0.00038 |
| IP27 | 4a | γ/1 | 2.7 | 16* |
| IP72 | 4a | γ/1 | 2.8 | 4.4* |
| IP14 | 4b | γ/1 | 2.6 | 81 |
| IP82 | 4b | γ/1 | 2.7 | 11* |
| IP86 | 4b | γ/1 | 2.9 | 0.41* |
| IP13 | 5 | γ/1 | 2.6 | 1.2 |
| IP20 | 5 | γ/1 | 2.3 | 0.1 |
| IP21 | 5 | γ/1 | 2.8 | 1.50 |
| IP28 | 5 | γ/1 | 2.2 | 1.70 |
| IP8 | 5 | γ/1 | 2.4 | 0.93 |
| IP25 | 5 | γ/1 | 2.7 | 1.90 |
| IP55 | 5 | γ/1 | 2.8 | 1.10 |
| IP4 | 6a | γ/1 | 2.5 | 0.13* |
| IP19 | 6a | γ/1 | 2.6 | 3.70 |
| IP24 | 6a | γ/1 | 2.3 | 5.4* |
| IP40 | 6a | γ/1 | 2.7 | 2.9 |
| IP87 | 6a | γ/1 | 2.8 | 2.3* |
| IP6 | 6b | γ/1 | 2.4 | 0.13* |
| IP30 | 6b | γ/1 | 2.8 | 0.044* |
| IP12 | 6b | γ/1 | 2.4 | 0.82 |
| IP54 | 7 | γ/1 | 2.9 | 2.0* |
| IP73 | 7 | γ/1 | 2.9 | 4.8 |
| IP46 | 7 | γ/1 | 2.7 | 2.2* |
| IP52 | 7 | γ/1 | 2.8 | 6.8* |
| IP69 | 7 | γ/1 | 2.5 | 0.12* |
| IP74 | 7 | γ/1 | 2.8 | 6.5* |

*Complex binding analysis

TABLE 3

Activities of Mutants of PE38 with Single Amino Acid Changes.

| HA22 IT | Relative Activity (%) |
|---|---|
| WT | 100 |
| P290A | 58 |
| R313A | 133 |
| N314A | 42 |
| D324A | 133 |
| E327A | 117 |
| E331A | 144 |
| Q332A | 176 |
| D403A | 19 |
| E431A | 140 |
| R432A | 194 |
| R458A | 63 |
| R467A | 93 |
| R490A | 150 |
| R505A | 144 |
| R513A | 106 |
| L516A | 140 |
| R538A | 188 |
| E548A | 23 |
| R576A | 100 |
| K590Q | 120 |

(Note:
They Are All Quite Active)

TABLE 4

IC$_{50}$s of Immunotoxins Made Mutating PE at Residues that Affect Binding to Different Epitopes

| IT with designated residues mutated in PE sequence | Epitope | # of Mabs in this epitope group | # of Mabs blocked by mutating this residue | Assay #1 | Assay #2 | Assay #3 | Assay #4 | Assay #5 | Assay #6 | Assay #7 | Assay #8 | Assay #9 | Assay #10 | Assay #11 | Assay #12 | Assay #13 | Assay #14 |
|---|---|---|---|---|---|---|---|---|---|---|---|---|---|---|---|---|---|
| HA22 immunotoxin (control) | | 37 | | 1.2 ng/ml | 1.0 | 1.0 | 3.4 | 3.3 | 4 | 0.2 | 2.0 | 0.7 | 0.9 | 1.0 | 1.8 | 0.44 | 0.7 |
| N314A* | 1 | 8 | 8 | 3.0 | 2.0 | | | | | | | | | | | | |
| N314S | 1 | | 8 | | 1.1 | | | | | | | | | | | | |
| Q332A | 1 | | 8 | 0.72 | | | | | | | | | | | | | |
| R467A | 2c | 3 | 3 | 0.72 | | | | | | | | | | | | | |
| R490A | 5 | 3 | 3 | 1.5 | | | | 3.7 | | | | | | | | | |
| R538A* | 2c | | 3 | 2.1 | | | | | | | | | | | | | |
| Q332A R490A | 1/5/7/ | | | | 3.0 | | | | | | 1.9 (?) | | | | | | |
| K590A/K606A/613del* | | | | | | | | | | | | | | | | | |
| K590A | 7 | 3 | 3 | | | 1.0 | | | | | | | | | | | |
| R490A K590A* | 5/7 | 3/3 | 3/3 | | | | 4.5 | 4.2 | 5 | | 4.4 | | 0.7 | | | | |
| Q332A R490A* | 5/1 | | 5 | | | | | 6.5 | 10 | | | | | | | | |
| K606A* | | | | | | | | | | 0.45 | | | | | | | |
| R490A R538A | 5/2/7 | | | | | | | | | | 5.0/6.2 | | | | | | |
| K590A* | | | | | | | | | | | | | | | | | |
| Q332S | 1 | 8 | 17 | | | | | | | | | 0.55 | | | | | |
| R490S* | 5 | 3 | | | | | | | | | | 30 | 0.7 | | | | |
| R538S* | 2 | 3 | | | | | | | | | | >100 | | | | | |
| K590S | 7 | 3 | | | | | | | | | | 0.4 | | | | | |
| Q332S R467A R490A K590S | 1/2c/5/7 | | 17 | | | | | | | | | | 0.8 | 0.75 | | | |
| R313A Q332S R467A R490A K590S | 3/1/2c/5/7 | (5) | 22 | | | | | | | | | | | 0.6 | 1.0 | | |
| R313A Q332S R432G K590S | 3/1/ | 6 | 5 | | | | | | | | | | | | 0.8 | | |
| R467A R490A K590S | 4a/2c/5/7 | | | | | | | | | | | | | | | | |
| R313A Q332S R432G | 3/1/ | | | | | | | | | | | | | | | | |
| R467A R490A R513A K590S | 4a/2c/5/6/7 | | | | | | | | | | | | | | | .7 | |
| R313A Q332S R432G | 3/1/ | | | | | | | | | | | | | | | 0.9 | |
| R467A R490A R513A | 4a/2c/5/6/ | | | | | | | | | | | | | | | | |
| E548S K590S | 6/7 | | | | | | | | | | | | | | | | 0.8 |

*/Mutation(s) reduced cytotoxicity by more than 50%

While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited herein are incorporated by reference in their entirety for all purposes to the same extent as if each individual publication or patent document were individually denoted to be incorporated. Citation of various references in this document is not an admission that any particular reference is considered to be "prior art" to the invention.

What is claimed is:

1. An isolated *Pseudomonas* exotoxin A ("PE") comprising a PE amino acid sequence, wherein one or more of amino acid residues N314, D324, Q332, D403, R412, R427, E431, R432, R458, D461, R467, R505, R538, E548, R576, K590, and L597 as defined by reference to SEQ ID NO: 1 are, independently, substituted, provided that when amino acid residue Q332 is substituted, amino acid residue Q332 is substituted with a anine, glycine, or serine;

when amino acid residue K590 is substituted, amino acid residue K590 is substituted with alanine, glycine, or serine;

when amino acid residue L597 is substituted, amino acid residue L597 is substituted with glycine, serine or glutamine; and when one or more of amino acid residues N314, D324, D403, R412, R427, E431, R432, R458, D461, R467, R505, R538, E548, and R576 are substituted, the one or more of amino acid residues N314, D324, D403, R412, R427, E431, R432, R458, D461, R467, R505, R538, E548, and R576 are, independently, substituted with alanine, glycine, serine or glutamine;

wherein the PE optionally has a further substitution of amino acid residue R490, as defined by reference to SEQ ID NO: 1, with alanine, valine, glycine, leucine, isoleucine or glutamine, and wherein the PE optionally has a further substitution of, independently, one or more of amino acid residues E282, E285, P290, R313, P319, E327, E331, R513, E522, and R551, as defined by reference to SEQ ID NO: 1, with alanine, glycine, serine or glutamine.

2. The PE of claim 1, wherein one or more of amino acid residues N314, D324, Q332, D403, E431, R432, R458, R467, R505, R538, E548, R576, K590, and L597 are, independently, substituted provided that when amino acid residue Q332 is substituted, amino acid residue Q332 is substituted with alanine, glycine, or serine;

when amino acid residue K590 is substituted, amino acid residue K590 is substituted with alanine, glycine, or serine;

when amino acid residue L597 is substituted, amino acid residue L597 is substituted with glycine, serine or glutamine; and when one or more of amino acid residues N314, D324, D403, E431, R432, R458, R467, R505, R538, E548, and R576 are substituted, the one or more of amino acid residues N314, D324, D403, E431, R432, R458, R467, R505, R538, E548, and R576 are, independently, substituted with alanine, glycine, serine or glutamine;

wherein the PE optionally has a further substitution of amino acid residue R490, as defined by reference to SEQ ID NO: 1, with alanine, valine, glycine, leucine, isoleucine or glutamine, and wherein the PE optionally has a further substitution of, independently, one or more of amino acid residues P290, R313, E327, E331, and R513, as defined by reference to SEQ ID NO: 1, with alanine, glycine, serine or glutamine.

3. The PE of claim 1, wherein one or more of amino acid residues N314, D324, Q332, R432, R467, R538, and K590 are, independently, substituted provided that when amino acid residue Q332 is substituted, amino acid residue Q332 is substituted with alanine, glycine, or serine;

when amino acid residue K590 is substituted, amino acid residue K590 is substituted with alanine, glycine, or serine; and when one or more of amino acid residues N314, D324, R432, R467, and R538 are substituted, the one or more of amino acid residues N314, D324, R432, R467, and R538 are, independently, substituted with alanine, glycine, serine or glutamine;

wherein the PE optionally has a further substitution of, independently, one or more of amino acid residues R313, E327, and E331, as defined by reference to SEQ ID NO: 1, with alanine, glycine, serine or glutamine.

4. The PE of claim 1, wherein one or more of amino acid residues N314, D324, Q332, D403, R412, R427, E431, R432, R458, D461, R467, R505, R538, E548, R576, K590, and L597 are, independently, substituted provided that when amino acid residue L597 is substituted amino acid residue L597 is substituted with glycine or serine; and when one or more of amino acid residues N314, D324, Q332, D403, R412, R427, E431, R432, R458, D461, R467, R505, R538, E548, R576, and K590 substituted, the one or more of amine acid residues N314, D324, Q332, D403, R412, R427, R431, R432, R458, D461, R467, R505, R538, E548, R576, and K590 are, independently substituted with alanine, glycine, serine;

wherein the PE optionally has a further substitution of amino acid residue R490, as defined by reference to SEQ ID NO: 1, with alanine, valine, glycine, leucine, isoleucine or glutamine, and wherein the PE optionally has a further substitution of, independently, one or more of amino acid residues E282, E285, P290, R313, P319, E327, E331, R513, E522, and R551, as defined by reference to SEQ ID NO: 1, with alanine, glycine, or serine.

5. The PE of claim 1, wherein one or more of amino acid residues N314, D324, Q332, D403, R412, R427, E431, R432, R458, D461, R467, R505, R538, E548, R576, and K590 are, independently, substituted with alanine, wherein the PE optionally has a further substitution of amino acid residue R490, as defined by reference to SEQ ID NO: 1, with alanine, valine, glycine, leucine, isoleucine or glutamine, and wherein the PE optionally has a further substitution of, independently, one or more of amino acid residues E282, E285, P290, R313, R319, E327, E331, R513, E522, R551, and L597, as defined by reference to SEQ ID NO: 1, with alanine.

6. The PE of claim 1, wherein two or more of amino acid residues N314, D324, Q332, D403, R412, R427, E431, R432, R458, D461, R467, R505, R538, E548, R576, K590, and L597 as defined by reference to SEQ ID NO: 1 are, independently, substituted, wherein the PE optionally has a further substitution of amino acid residue R490, as defined by reference to SEQ ID NO: 1, with alanine, valine, glycine, leucine, isoleucine or glutamine wherein the PE optionally has a further substitution of, independently, one or more of amino acid residues E282, E285, P290, R313, P319, E327, E331, R513, E522, and R551, as defined by reference to SEQ ID NO: 1.

7. The PE of claim 6, wherein the PE comprises substitutions R313A, Q332S, R432G, R467A, R490A, R513A, E548S, and K590S.

8. The PE of claim 1, wherein the PE has a further substitution of amino acid residue R490 with alanine, valine, glycine, leucine, isoleucine or glutamine.

9. The PE of claim 8, wherein the PE has a further substitution of amino acid residue R490 with alanine.

10. The PE of claim 8, wherein amino acid residues Q332, R490, R467, and K590 are, independently; substituted, wherein the PE optionally has a further substitution of, independently, one or more of amino acid residues R313, R432, R513, and E548.

11. The PE of claim 10, wherein the PE has the further substitution of amino acid residue R313.

12. The PE of claim 11, wherein the PE has the further substitution of amino acid residue R432.

13. The PE of claim 10, wherein the PE has the further substitution of amino acid residue R513.

14. The PE of claim 10, wherein the PE has the further substitution of amino acid residue E548.

15. The PE of claim 1, wherein the PE is selected from the group consisting of PE35, PE38, PE38 KDEL, PE40, PE4E, and PE38QQR.

16. The PE according to claim 1, wherein one or more of amino acid residues R427, R458, R467, R505, R538, R432, and E548 are, independently, substituted with alanine, glycine, serine, or glutamine, wherein the PE optionally has a further substitution of amino acid residue R490, as defined by reference to SEQ ID NO: 1, with alanine, valine, glycine, leucine, isoleucine or glutamine, and wherein the PE optionally has a further substitution of amino acid residue R513 with alanine, glycine, serine, or glutamine.

17. The PE according to claim 16, wherein the PE has the further substitution of amino acid residue R490 with alanine, valine, glycine, leucine, isoleucine or glutamine.

18. The PE of claim 17, wherein amino acid residue R490 is substituted with alanine.

19. The PE according to claim 16, wherein one or more of amino acid residues R427, R458, R467, R505, and R538 are, independently, substituted with alanine, glycine, serine, or glutamine, wherein the PE optionally has a further substitution of amino acid residue R490, as defined by reference to SEQ ID NO: 1, with alanine, valine, glycine, leucine, isoleucine or glutamine.

20. The PE according to claim 16, wherein one or more of amino acid residues R432 and E548 are, independently, substituted with alanine, glycine, or serine, wherein the PE optionally has a further substitution of amino acid residue R513 with al anine, glycine, or serine.

21. The PE of claim 1, wherein amino acid residues R427, R458, R467, R490, R505 and R538 are, independently, substituted.

22. The PE of claim 1, wherein amino acid residues R432, R467, R490, R513, E548 and K590 are, independently, substituted.

23. The PE of claim 1, wherein one or more of amino acid residues R432, R467, E548 and K590 are, independently, substituted, and the PE has a further substitution of amino acid residue R490 with alanine, valine, glycine, leucine, isoleucine or glutamine, wherein the PE optionally as a further substitution of amino acid residue R513.

24. The PE of claim 1, wherein one or more of amino acid residues R427, R458, R467, R505 and R538 are, independently, substituted, and the PE has a further substitution of amino acid residue R490 with alanine, valine, glycine, leucine, isoleucine or glutamine.

25. The PE of claim 1, wherein one or more of R427, R467, R505, and R538 are, independently, substituted with alanine, glycine, serine, or glutamine, wherein the PE optionally has a further substitution of amino acid residue R490, as defined by reference to SEQ ID NO: 1, with alanine, valine, glycine, leucine, isoleucine or glutamine, and wherein the PE optionally has a further substitution of, independently, one or more of amino acid residues E282, E285, P290, R313, N314, P319, D324, E327, E331, Q332, D403, R412, E431, R432, R458, D461, R513, E522, E548, R551, R576, K590, and L597, as defined by reference to SEQ ID NO: 1, with alanine, glycine, serine or glutamine.

26. A chimeric molecule comprising
(a) a targeting moiety conjugated or fused to
(b) a *Pseudomonas* exotoxin A ("PE") comprising a PE amino acid sequence, wherein one or more of amino acid residues N314, D324, Q332, D403, R412, R427, E431, R432, R458, D461, R467, R505, R538, E548, R576, K590, and L597 as defined by reference to SEQ ID NO: 1 are, independently, substituted provided that when amino acid residue Q332 is substituted, amino acid residue Q332 is substituted with alanine, valine, glycine, leucine, or isoleucine;

when amino acid residue K590 is substituted, amino acid residue K590 is substituted with alanine, glycine, leucine, or isoleucine; and when one or more of amino acid residues N314, D324, D403, R412, R427, E431, R432, R458, D461, R467, R505, R538, E548, R576, and L597 are substituted, the one or more of amino acid residues N314, D324, D403, R412, R427, E431, R432, R458, D461, R467, R505, R538, E548, R576, and L597 are, independently substituted with alanine, valine, glycine, leucine, isoleucine or glutamine;

wherein the PE optionally has a further substitution of amino acid residue R490, as defined by reference to SEQ ID NO: 1, with alanine, valine, glycine, leucine, isoleucine or glutamine, and wherein the PE optionally has a further substitution of, independently, one or more of amino acid residues E282, E285, P290, R313, P319, E327, E331, R513, E522, and R551, as defined by reference to SEQ ID NO: 1, with alanine, valine, glycine, leucine, isoleucine or glutamine.

27. The chimeric molecule of claim 26, wherein the PE is selected from the group consisting of PE35, PE38, PE38 KDEL, PE40, PE4E, and PE38QQR.

28. The chimeric molecule of claim 26, wherein one or more of amino acid residues N314, D324, Q332, D403, E431, R432, R458, R467, R505, R538, E548, R576, K590, and L597 are, independently, substituted, wherein the PE optionally has a further substitution of amino acid residue R490, as defined by reference to SEQ ID NO: 1, with alanine, valine, glycine, leucine, isoleucine or glutamine, and wherein the PE optionally has a further substitution of independently, one or more of amino acid residues P290, R313, E327, E331, and R513, as defined by reference to SEQ ID NO: 1.

29. The chimeric molecule of claim 26, wherein one or more of amino acid residues N314, D324, Q332, R432, R467, R538, and K590 are, independently, substituted, wherein the PE optionally has a further substitution of, independently, one or more of amino acid residues R313, E327, and E331, as defined by reference to SEQ ID NO: 1.

30. The chimeric molecule of claim 26, wherein one or more of amino acid residues N314, D324, Q332, D403, R412, R427, E431, R432, R458, D461, R467, R505, R538, E548, R576, K590, and L597 are, independently, substituted with alanine or glycine, wherein the PE optionally has a further substitution of amino acid residue R490, as defined by reference to SEQ ID NO: 1, with alanine, glycine, leucine, isoleucine or glutamine, and wherein the PE optionally has a further substitution of, independently, one or more of amino acid residues E282, E285, P290, R313, P319, E327, E331, R513, E522, and R551, as defined by reference to SEQ ID NO: 1, with alanine or glycine.

31. The chimeric molecule of claim 26, wherein one or more of amino acid residues N314, D324, Q332, D403, R412, R427, E431, R432, R458, D461, R467, R505, R538, E548, R576, K590, and L597 are, independently, substituted with alanine, wherein the PE optionally has a further substitution of amino acid residue R490, as defined by reference to SEQ ID NO: 1, with alanine, valine, glycine, leucine, isoleucine or glutamine, wherein the PE optionally has a further substitution of, independently, one or more of amino acid residues E282, E285, P290, R313, P319, E327, E331, R513, E522, and R551, as defined by reference to SEQ ID NO: 1, with alanine.

32. The chimeric molecule of claim 26, wherein the PE has a further substitution of amino acid residue R490 with alanine, valine, glycine, leucine, isoleucine or glutamine.

33. The chimeric molecule of claim 26, wherein the PE has a further substitution of amino acid residue R490 with alanine.

34. The chimeric molecule of claim 26, wherein the targeting moiety is an antibody.

35. The chimeric molecule of claim 34, wherein the antibody is an anti-CD22 antibody.

36. The chimeric molecule of claim 34, wherein the antibody is an anti-mesothelin antibody.

37. The chimeric molecule of claim 26, wherein the antibody is selected from the group consisting of an scFv, a dsFv, a Fab, and a F(ab')$_2$.

38. The chimeric molecule of claim 26, wherein amino acid residues Q332, R490, R467, and K590 are, independently, substituted, and wherein the PE optionally has a further substitution of one or more of amino acid residues R313, R432, R513, and E548.

39. The chimeric molecule of claim 26, wherein the PE has a further substitution of amino acid residue R313.

40. The chimeric molecule of claim 26, wherein the PE has a further substitution of amino acid residue R432.

41. The chimeric molecule of claim 40, wherein the PE has a further substitution of amino acid residue R513.

42. The chimeric molecule of claim 40, wherein the PE has a further substitution of amino acid residue E548.

43. The chimeric molecule of claim 40, wherein the PE comprises the substitutions R313A, Q332S, R432G, R467A, R490A, R513A, E548S, and K590S.

44. The chimeric molecule of claim 26, wherein the targeting moiety is a cytokine.

45. The chimeric molecule of claim 26, wherein one or more of amino acid residues R427, R458, R467, R505, R538, R432, and E548 are, independently, substituted with alanine, glycine, serine, or glutamine, wherein the PE optionally has a further substitution of amino acid residue R490, as defined by reference to SEQ ID NO: 1, with alanine, valine, glycine, leucine, isoleucine or glutamine, and wherein the PE optionally has a further substitution of amino acid residue R513 with alanine, glycine, serine, or glutamine.

46. The chimeric molecule according to claim 45, wherein the PE has the further substitution of amino acid residue R490 with alanine, valine, glycine, leucine, isoleucine or glutamine.

47. The chimeric molecule of claim 46, wherein the PE has the further substitution of amino acid residue R490 with alanine.

48. The chimeric molecule according to claim 45, wherein one or more of amino acid residues R427, R458, R467, R505, and R538 are, independently, substituted with alanine, glycine, serine, or glutamine, wherein the PE optionally has a further substitution of amino acid residue R490, as defined by

51 reference to SEQ ID NO: 1, with alanine, valine, glycine, leucine, isoleucine or glutamine.

49. The chimeric molecule according to claim 45, wherein one or more of amino acid residues R432, and E548 are, independently, substituted with alanine, glycine, serine, or glutamine, wherein the PE optionally has a further substitution of amino acid residue R513 with alanine, glycine, serine, or glutamine.

50. The chimeric molecule of claim 26, wherein amino acid residues R432, R467, R490, R513, E548 and K590 are, independently, substituted.

51. The chimeric molecule of claim 26, wherein amino acid residues R427, R458, R467, R490, R505 and R538 are, independently, substituted.

52. The chimeric molecule of claim 36, wherein the targeting moiety is the targeting moiety of SS1P.

53. The chimeric molecule of claim 35, wherein the targeting moiety is the targeting moiety of BL22.

54. The chimeric molecule of claim 35, wherein the targeting moiety is the targeting moiety of HA22.

55. The chimeric molecule of claim 26, wherein one or more of amino acid residues R432, R467, E548 and K590 are, independently, substituted, and the PE has a further substitution of amino acid residue R490 with alanine, glycine, leucine, isoleucine or glutamine, wherein the PE optionally has a further substitution of amino acid residue R513.

56. The chimeric molecule of claim 26, wherein one or more of amino acid residues R427, R458, R467, R505 and R538 are, independently, substituted, and the PE has a further substitution of amino acid residue R490 with alanine, valine, glycine, leucine, isoleucine or glutamine.

57. The chimeric molecule of claim 26, wherein one or more of R427, R467, R505, and R538 are, independently, substituted with alanine, valine, glycine, leucine, isoleucine, or glutamine,
wherein the PE optionally has a further substitution of amino acid residue R490, as defined by reference to SEQ ID NO: 1, with alanine, valine, glycine, leucine, isoleucine or glutamine, and
wherein the PE optionally has a further substitution of, independently one or more of amino acid residues E282, E285, P290, R313, N314, P319, D324, E327, E331, Q332, D403, R412, E431, R432, R458, D461, R513, E522, E548, R551, R576, K590, and L597, as defined by reference to SEQ ID NO: 1, with alanine, valine, glycine, leucine, isoleucine, uz glutamine.

58. A composition comprising
(a) a chimeric molecule comprising a targeting moiety conjugated or fused to a *Pseudomonas* exotoxin A ("PE") comprising a PE amino acid sequence, wherein one or more of amino acid residues N314, D324, Q332, D403, R412, R427, E431, R432, R458, D461, R467, R505, R538, E548, R576, K590, and L597 as defined by reference to SEQ ID NO: 1 are, independently, substituted, provided that
when amino acid residue Q332 is substituted, amino acid residue Q332 is substituted with alanine, valine, glycine, leucine, or isoleucine;
when amino acid residue K590 is substituted, amino acid residue K590 is substituted with alanine, glycine, leucine, or isoleucine, and
when one or more of amino acid residues N314, D324, D403, R412, R427, E431, R432, R458, D461, R467, R505, R538, E548, R576, and L597 are substituted, the one or more of amino acid residues N314, D324, D403, R412, R427, E431, R432, R458, D461, R467, R505,

52

R538, E538, R576, and L597 are, independently, substituted with alanine, valine, glycine, leucine, isoleucine, or glutamine;
wherein the PE optionally has a further substitution of amino acid residue R490, as defined by reference to SEQ ID NO: 1, with alanine, valine, glycine, leucine, isoleucine, or glutamine, and
wherein the PE optionally has a further substitution of independently, one or more of amino acid residues E282, E285, P290, R313, P319, E327, E331, R513, E522, and R551, as defined by reference to SEQ ID NO: 1, with alanine, valine, glycine, leucine, isoleucine or glutamine, and
(b) a pharmaceutically acceptable carrier.

59. The composition of claim 58, wherein the PE is selected from the group consisting of PE35, PE38, PE38KDEL, PE40, PE4E, and PE38QQ.

60. The composition of claim 58, wherein one or more of amino acid residues N314, D324, Q332, D403, E431, R432, R458, R467, R505, R538, E548, R576, K590, and L597 are, independently, substituted,
wherein the PE optionally has a further substitution of amino acid residue R490, as defined by reference to SEQ ID NO: 1, with alanine, valine, glycine, leucine, isoleucine or glutamine, and
wherein the PE optionally has a further substitution of, independently, one or more of amino acid residues P290, R313, E327, E331, and R513, as defined by reference to SEQ ID NO: 1.

61. The composition of claim 58, wherein one or more of amino acid residues N314, D324, Q332, R432, R467, R538, and K590 are, independently, substituted, wherein the PE optionally has a further substitution of, independently, one or more of amino acid residues R313, E327, and E331, as defined by reference to SEQ ID NO: 1.

62. The composition of claim 58, wherein one or more of amino acid residues N314, D324, Q332, D403, R412, R427, E431, R432, R458, D461, R467, R505, R538, E548, R576, K590, and L597 are, independently, substituted with alanine or glycine,
wherein the PE optionally has a further substitution of amino acid residue R490, as defined by reference to SEQ ID NO: 1, with alanine, glycine, leucine, isoleucine or glutamine, and
wherein the PE optionally has a further substitution of, independently, one or more of amino acid residues E282, E285, P290, R313, P319, E327, E331, R513, E522, and R551 as defined by reference to SEQ ID NO: 1, with alanine or glycine.

63. The composition claim 58, wherein one or more of amino acid residues N314, D324, Q332, D403, R412, R427, E431, R432, R458, D461, R467, R505, R538, E548, R576, K590, and L597 are, independently, substituted with alanine,
wherein the PE optionally has a further substitution of amino acid residue R490, as defined by reference to SEQ ID NO: 1, with alanine, valine, glycine, leucine, isoleucine or glutamine, and
wherein the PE optionally has a further substitution of, independently, one or more of amino acid residues E282, E285, P290, R313, P319, E327, E331, R513, E522, and R551, as defined by reference to SEQ ID NO: 1, with alanine.

64. The composition of claim 58, wherein the PE of the chimeric molecule has a further substitution of amino acid residue R490 with alanine, valine, glycine, leucine, isoleucine or glutamine.

65. The composition of claim 58, wherein amino acid residues Q332, R490, R467, and K590 are, independently, substituted and the PE optionally has a further substitution of one or more of amino acid residues R313, R432, R513, and E548.

66. The composition of claim 65, wherein the PE has a further substitution of amino acid residue R313.

67. The composition of claim 65, wherein the PE has a further substitution of amino acid residue R432.

68. The composition of claim 65, wherein the PE has a further substitution of amino acid residue R513.

69. The composition of claim 65, wherein the PE has a further substitution of amino acid residue E548.

70. The composition of claim 65, wherein the PE comprises the substitutions R313A, Q332S, R432G, R467A, R490A, R513A, E548S, and K590S.

71. The composition of claim 58, wherein one or more of amino acid residues R427, R458, R467, R505, R538, R432, or E548 are, independently, substituted with alanine, glycine, serine, or glutamine,
wherein the PE optionally has a further substitution of amino acid residue R490, as defined by reference to SEQ ID NO: 1, with alanine, valine, glycine, leucine, isoleucine or glutamine, and
wherein the PE optionally has a further substitution of amino acid residue R513 with alanine, glycine, serine, or glutamine.

72. The composition of claim 71, wherein the PE has the further substitution of amino acid residue R490 with alanine, valine, glycine, leucine, isoleucine or glutamine.

73. The composition of claim 72, wherein amino acid residue R490 is substituted with alanine.

74. The composition according to claim 72, wherein one or more of amino acid residues R427, R458, R467, R505, and R538 are, independently, substituted with alanine, glycine, serine, or glutamine, wherein the PE optionally has a further substitution of amino acid residue R490, as defined by reference to SEQ ID NO: 1, with alanine, valine, glycine, leucine, isoleucine or glutamine.

75. The composition according to claim 71, wherein one or more of amino acid residues R432 and E548 are, independently, substituted with alanine, glycine, serine, or glutamine, wherein the PE optionally has a further substitution of amino acid residue R513 with alanine, glycine, serine, or glutamine.

76. The composition of claim 58, wherein amino acid residues R432, R467, R490, R513, E548 and K590 are, independently, substituted.

77. The composition of claim 58, wherein amino acid residues R427, R458, R467, R490, R505 and R538 are, independently, substituted.

78. The composition of claim 58, wherein the targeting moiety is an anti-CD22 antibody.

79. The composition of claim 58, wherein the targeting moiety is the targeting moiety of SS1P.

80. The composition of claim 58, wherein the targeting moiety is the targeting moiety of BL22.

81. The composition of claim 58, wherein the targeting moiety is the targeting moiety of HA22.

82. The composition of claim 58, wherein one or more of amino acid residues R432, R467, E548 and K590 are, independently, substituted, and the PE has a further substitution of amino acid residue R490 with alanine, valine, glycine, leucine, isoleucine or glutamine, wherein the PE optionally has a further substitution of amino acid residue R513.

83. The composition of claim 58, Wherein one or more of amino acid residues R427, R458, R467, R505 and R538 are, independently, substituted, and the PE has a further substitution of amino acid residue R490 with Janine, valine, glycine, leucine, isoleucine or glutamine.

84. The composition of claim 58, wherein one or more of R427, R467, R505, and R538 are, independently, substituted with alanine, valine, glycine, leucine, isoleucine, or glutamine,
wherein the PE optionally has a further substitution of amino acid residue R490, as defined by reference to SEQ ID NO: 1, with alanine, valine, glycine, leucine, isoleucine or glutamine, and
wherein the PE optionally has a further substitution of, independently, one or more of amino acid residues E282, E285, P290, R313, N314, P319, D324, E327, E331, Q332, D403, R412, E431, R432, R458, D461, R513, E522, E548, R551, R576, K590, and L597, as defined by reference to SEQ ID NO: 1, with alanine, valine, glycine, leucine, isoleucine, or glutamine.

85. The composition of claim 58, wherein the targeting moiety is an anti-mesothelin antibody.

86. A method of inhibiting the growth of a cell bearing a target molecule, the method comprising contacting the cell with a chimeric molecule comprising a targeting moiety that specifically binds the target molecule, and a *Pseudomonas exotoxin* A ("PE") comprising a PE amino acid sequence, wherein one or more of amino acid residues N314, D324, Q332, D403, R412, R427, E431, R432, R458, D461, R467, R505, R538, E548, R576, K590, and L597 as defined by reference to SEQ ID NO: 1 are, independently, substituted provided that
when amino acid residue Q332 is substituted, amino acid residue Q332 is substituted with alanine, valine, glycine, leucine, or isoleucine;
when amino acid residue K590 is substituted, amino acid residue K590 is substituted with alanine, valine, glycine, leucine, or isoleucine; and
when one or more of amino acid residues N314, D324, D403, R412, R427, E431, R432, R458, D461, R467, R505, R538, E548, R576, and L597 are substituted, the one or more of amino acid residues N314, D324, D403, R412, R427, E431, R432, R458, D461, R467, R505, R538, E548, R576, and L597 are, independently, substituted with alanine, valine, glycine, leucine, isoleucine, or glutamine;
wherein the PE optionally has a further substitution of amino acid residue R490, as defined by reference to SEQ ID NO: 1, with alanine, valine, glycine, leucine, isoleucine, or glutamine, and
wherein the PE optionally has a further substitution of, independently, one or more of amino acid residues E282, E285, P290, R313, P319, E327, E331, R513, E522, and R551, as defined by reference to SEQ ID NO: 1, with alanine, valine, glycine, leucine, isoleucine glutamine,
wherein co acting the cell with the chimeric molecule inhibits the growth of the cell.

87. The method of claim 86, wherein the PE is selected from the group consisting of PE35, PE38, PE38 KDEL, PE40, PE4E, and PE38QQR.

88. The method of claim 86, wherein the target molecule is a cytokine receptor and the targeting moiety is a cytokine which binds to the receptor.

89. The method of claim 88, wherein the target molecule is an IL-13 receptor and the targeting molecule is an IL-13, a mutated IL-13, or a circularly permuted IL-13.

90. The method of claim 86, wherein the target molecule is an antigen and the targeting molecule is an antibody which specifically binds to the antigen.

91. The method of claim 90, wherein the antigen is a cancer antigen.

92. The method of claim 86, wherein amino acid residues Q332, R490, R467, and K590 are, independently, substituted, and the PE optionally has a further substitution of one or more of amino acid residues R313, R432, R513, and E548.

93. The method of claim 92, wherein the PE has a further substitution of amino acid residue R313.

94. The method of claim 92, wherein the PE has a further substitution of amino acid residue R432.

95. The method of claim 92, wherein the PE has a further substitution of amino acid residue R513.

96. The method of claim 92, wherein the PE has a further substitution of amino acid residue E548.

97. The method of claim 86, wherein amino acid residues R313A, Q332S, R432G, R467A, R490A, R513A, E548S, and K590S are, independently, substituted.

98. The method of claim 86, wherein amino acid residues R432, R467, R490, R513, E548 and K590 are, independently, substituted.

99. The method of claim 86, wherein amino acid residues R427, R458, R467, R490, R505 and R538 are, independently, substituted.

100. The method of claim 86, wherein the targeting moiety is an anti-CD22 antibody.

101. The method of claim 86, wherein the targeting moiety is the targeting moiety of SS1P.

102. The method of claim 86, wherein the targeting moiety is the targeting moiety of BL22.

103. The method of claim 86, wherein the targeting moiety is the targeting moiety of HA22.

104. The method of claim 86, wherein the targeting moiety is an anti-mesothelin antibody.

105. The method of claim 86, wherein one or more of R427, R467, R505, and R538 are, independently, substituted with alanine, valine, glycine, leucine, isoleucine, or glutamine,
   wherein the PE optionally has a further substitution of amino acid residue R490, as defined by reference to SEQ ID NO: 1, with alanine, valine, glycine, leucine, isoleucine or glutamine, and
   wherein the PE optionally has a further substitution of, independently, one or more of amino acid residues E282, E285, P290, R313, N314, P319, D324, E327, E331, Q332, D403, R412, E431, R432, R458, D461, R513, E522, E548, R551, R576, K590, and L597, as defined by reference to SEQ ID NO: 1, with alanine, valine, glycine, leucine, isoleucine, or glutamine.

* * * * *

SEQUENCE LISTING

```
<160> NUMBER OF SEQ ID NOS: 4

<210> SEQ ID NO 1
<211> LENGTH: 613
<212> TYPE: PRT
<213> ORGANISM: Pseudomonas aeruginosa
<220> FEATURE:
<223> OTHER INFORMATION: native Pseudomonas exotoxin A (PE)

<400> SEQUENCE: 1

Ala Glu Glu Ala Phe Asp Leu Trp Asn Glu Cys Ala Lys Ala Cys Val
 1               5                  10                  15

Leu Asp Leu Lys Asp Gly Val Arg Ser Ser Arg Met Ser Val Asp Pro
             20                  25                  30

Ala Ile Ala Asp Thr Asn Gly Gln Gly Val Leu His Tyr Ser Met Val
         35                  40                  45

Leu Glu Gly Gly Asn Asp Ala Leu Lys Leu Ala Ile Asp Asn Ala Leu
     50                  55                  60

Ser Ile Thr Ser Asp Gly Leu Thr Ile Arg Leu Glu Gly Gly Val Glu
 65                  70                  75                  80

Pro Asn Lys Pro Val Arg Tyr Ser Tyr Thr Arg Gln Ala Arg Gly Ser
                 85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300
```

```
Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
            325                 330                 335

Arg Leu Ala Leu Thr Leu Ala Ala Glu Ser Glu Arg Phe Val Arg
        340                 345                 350

Gln Gly Thr Gly Asn Asp Glu Ala Gly Ala Asn Ala Asp Val Val
            355                 360                 365

Ser Leu Thr Cys Pro Val Ala Ala Gly Glu Cys Ala Gly Pro Ala Asp
370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
            405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
            435                 440                 445

Ser Ile Val Phe Gly Gly Val Arg Ala Arg Ser Gln Asp Leu Asp Ala
450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
            485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
            515                 520                 525

Arg Leu Ile Gly His Pro Leu Pro Leu Arg Leu Asp Ala Ile Thr Gly
            530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
            565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
            595                 600                 605

Arg Glu Asp Leu Lys
        610

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:carboxyl
      terminus additional sequence, cytosol
      translocation sequence

<400> SEQUENCE: 2

Lys Asp Glu Leu
  1

<210> SEQ ID NO 3
<211> LENGTH: 4
```

```
<212> TYPE: PRT
<213> ORGANISM: Artificial Sequence
<220> FEATURE:
<223> OTHER INFORMATION: Description of Artificial Sequence:carboxyl
      terminus additional sequence, cytosol
      translocation sequence

<400> SEQUENCE: 3

Arg Glu Asp Leu
 1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence:native PE
      C-terminal sequence, residues 609-613

<400> SEQUENCE: 4

Arg Glu Asp Leu Lys
 1               5
```